US009938552B2

(12) United States Patent
Xu et al.

(10) Patent No.: US 9,938,552 B2
(45) Date of Patent: *Apr. 10, 2018

(54) METHODS OF SACCHARIFYING AND FERMENTING A CELLULOSIC MATERIAL

(71) Applicant: Novozymes A/S, Bagsvaerd (DK)

(72) Inventors: Hui Xu, Wake Forest, NC (US); Jesper Frickman, Youngsville, NC (US); Jiyin Liu, Raleigh, NC (US); Katja Salomon Johansen, Gentofte (DK); Hong Zhi Huang, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/026,486

(22) PCT Filed: Oct. 31, 2014

(86) PCT No.: PCT/US2014/063460
§ 371 (c)(1),
(2) Date: Mar. 31, 2016

(87) PCT Pub. No.: WO2015/066492
PCT Pub. Date: May 7, 2015

(65) Prior Publication Data
US 2016/0215314 A1 Jul. 28, 2016

Related U.S. Application Data

(60) Provisional application No. 61/898,707, filed on Nov. 1, 2013.

(30) Foreign Application Priority Data

Aug. 13, 2014 (WO) ............... PCT/CN2014/084259

(51) Int. Cl.
C12N 9/42 (2006.01)
C12P 19/14 (2006.01)
C12P 19/02 (2006.01)
C12P 7/10 (2006.01)

(52) U.S. Cl.
CPC ............... *C12P 19/14* (2013.01); *C12P 7/10* (2013.01); *C12P 19/02* (2013.01); *C12P 2203/00* (2013.01); *Y02E 50/16* (2013.01)

(58) Field of Classification Search
CPC ................................ C12P 19/02; C12P 19/14
USPC ..................... 435/27, 99, 106, 209
See application file for complete search history.

(56) References Cited

U.S. PATENT DOCUMENTS

| 8,951,758 | B2 | 2/2015 | Yang et al. |
| 9,476,036 | B2 | 10/2016 | Shasky et al. |
| 2012/0083019 | A1 | 4/2012 | Baidyaroy et al. |
| 2013/0052698 | A1 | 2/2013 | Yang et al. |
| 2014/0342038 | A1 | 11/2014 | Lewis et al. |
| 2015/0315622 | A1* | 11/2015 | Frickmann ............ C12P 19/14 435/99 |

FOREIGN PATENT DOCUMENTS

| WO | 2010/029159 A1 | 3/2010 |
| WO | 2011/057140 A1 | 5/2011 |
| WO | 2012/024698 A1 | 2/2012 |
| WO | 2012/061517 A1 | 5/2012 |
| WO | 2012/130120 A1 | 10/2012 |
| WO | 2013/016115 A1 | 1/2013 |
| WO | 2014/072389 A1 | 5/2014 |
| WO | 2014/072390 A1 | 5/2014 |
| WO | 2014/072392 A1 | 5/2014 |
| WO | 2014/072393 A1 | 5/2014 |
| WO | 2014/072394 A1 | 5/2014 |
| WO | 2014/072395 A1 | 5/2014 |
| WO | 2014/130812 A1 | 8/2014 |
| WO | 2015/004098 A1 | 1/2015 |
| WO | 2015/004099 A1 | 1/2015 |

OTHER PUBLICATIONS

Kolstad et al., Science, vol. 330, pp. 219-222 (2010).
Leggio et al., Computational and Structural Biotechnology Journal, vol. 2 Issue 3, No. e201209019, pp. 1-8 (2012).
Phillips et al., ACS Chemical Biology, vol. 6, pp. 1399-1406 (2011).
Podkaminer et al., Biotechnology for Biofuels, vol. 5, No. 43, pp. 1-9 (2012).
Quinlan et al., PNAS, vol. 108, No. 37, pp. 15079-15084 (2011).

* cited by examiner

Primary Examiner — Tekchand Saidha
(74) Attorney, Agent, or Firm — Joshua Price

(57) ABSTRACT

The invention relates to methods of saccharifying a cellulosic material comprising subjecting the cellulosic material to a catalase and a cellulolytic enzyme composition comprising a GH61 polypeptide in the presence of dissolved oxygen at a concentration of greater than 10% of the saturation level. The invention also related to methods of producing desired fermentation products, such as ethanol, using a method including a saccharification step of the invention.

20 Claims, No Drawings

US 9,938,552 B2

METHODS OF SACCHARIFYING AND FERMENTING A CELLULOSIC MATERIAL

CROSS-REFERENCE TO RELATED APPLICATIONS

This application is a 35 U.S.C. 371 national application of international application no. PCT/US2014/063460 filed Oct. 31, 2014, which claims priority or the benefit under 35 U.S.C. 119 of international application no. PCT/CN2014/084259 filed Aug. 13, 2014 and U.S. provisional application no. U.S. 61/898,707 filed Nov. 1, 2013. The contents of these application are fully incorporated herein by reference.

REFERENCE TO A SEQUENCE LISTING

This application contains a Sequence Listing in computer readable form, which is incorporated herein by reference.

BACKGROUND

Cellulosic material provides an attractive platform for generating alternative energy sources to fossil fuels. The conversion of cellulosic material (e.g., from lignocellulosic feedstock) into biofuels has the advantages of the ready availability of large amounts of feedstock, the desirability of avoiding burning or land filling the materials, and the cleanliness of the biofuels (such as ethanol). Wood, agricultural residues, herbaceous crops, and municipal solid wastes have been considered as feedstocks for biofuel production. Once the cellulosic material is saccharified and converted to fermentable sugars, e.g., glucose, the fermentable sugars may be fermented by yeast into biofuel, such as ethanol.

New and improved enzymes and enzyme compositions have been developed over the past decade and made saccharification of pretreated cellulosic material more efficient. However, there is still a need for improving saccharification of pretreated cellulosic material and processes for producing biofuels.

SUMMARY OF THE INVENTION

Described herein are methods of saccharifying a cellulosic material into fermentable sugars. Also described are methods of producing fermentation products, such as ethanol, from a cellulosic material, such as a pretreated cellulosic material, by saccharification and fermentation.

In one aspect the invention relates to methods of saccharifying a cellulosic material comprising subjecting the cellulosic material to a catalase, a cellulolytic enzyme composition, and a GH61 polypeptide in the presence of dissolved oxygen at a concentration of at least 0.5% of the saturation level.

In another aspect the invention relates methods of producing a fermentation product, comprising:

(a) subjecting a cellulosic material to a catalase, a cellulolytic enzyme composition, and a GH61 polypeptide in the presence of dissolved oxygen at a concentration of at least 0.5% of the saturation level;

(b) fermenting the saccharified cellulosic material with one or more fermenting microorganisms; and (c) optionally recovering the fermentation product from (b).

In an embodiment the cellulosic material has been pretreated e.g., by chemical and/or physical pretreatment, such as dilute acid and/or steam explosion pretreatment. In an embodiment the cellulosic material is unwashed, such as unwashed pretreated corn stover (uwPCS).

Methods of the present invention are used to saccharify/hydrolyze a pretreated cellulosic material to sugars. These sugars may be converted to many useful desired substances, e.g., fuel, potable ethanol, and/or fermentation products (e.g., acids, alcohols, ketones, gases, and the like).

The saccharified pretreated cellulosic material may be sugars that can be used in processes for producing syrups (e.g., High Fructose Corn Syrups (HFCS) and/or plastics (e.g., polyethylene, polystyrene, and polypropylene), polylactic acid (e.g., for producing PET).

Definitions

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 microliters for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 micromole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from Chaetomium thermophilum var. coprophilum: production, purification and some biochemical properties, J. Basic Microbiol. 42: 55-66. One unit of beta-glucosidase is defined as 1.0 micromole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. For purposes of the present invention, one unit of beta-xylosidase is defined as 1.0 micromole of p-nitrophenolate anion produced per minute at 40° C., pH 5 from 1 mM p-nitrophenyl-beta-D-xyloside as substrate in 100 mM sodium citrate containing 0.01% TWEEN® 20.

Biomass material: The term "biomass material" refers to any sugar-containing biomass (e.g., stems, leaves, hulls, husks, and cobs of plants or leaves, branches, and wood of trees) and any component thereof, such as cellulose, hemicellulose, or lignan. It is understood that, unless otherwise specified, biomass material includes untreated, pretreated, and hydrolyzed or partially hydrolyzed forms (e.g., biomass degraded products, such as oligosaccharides).

Catalase: The term "catalase" means a hydrogen-peroxide: hydrogen-peroxide oxidoreductase (E.C. 1.11.1.6 or E.C. 1.11.1.21) that catalyzes the conversion of two hydrogen peroxides to oxygen and two waters. Catalase activity can be determined by monitoring the degradation of hydrogen peroxide at 240 nm based on the following reaction:

$$2H_2O_2 \to 2H_2O + O_2$$

The reaction is conducted in 50 mM phosphate pH 7 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Cellulolytic enzyme composition: The term "cellulolytic enzyme composition" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., 2006, Outlook for cellulase improvement: Screening and selection strategies, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis/saccharification of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., 60° C., or 65° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., 60° C., or 65° C., 72 hours, sugar analysis by AMINEX® HPX-87H column (Bio-Rad Laboratories, Inc., Hercules, Calif., USA).

Cellulosic material: The term "cellulosic material" refers to any biomass material containing cellulose (a chemically homogeneous oligosaccharide or polysaccharide of beta-(1-4)-D-glucan (polymer containing beta (1-4) linked D-glucose units)). Although generally polymorphous, cellulose can be found in plant tissue primarily as an insoluble crystalline matrix of parallel glucan chains. Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). Cellulosic material includes any form of cellulose, such as polysaccharides degraded or hydrolyzed to oligosaccharides. It is understood herein that the cellulose may be in the form of a component of lignocellulose, a plant cell wall material containing lignin, cellulose, and hemicellulose in a mixed matrix.

In one aspect, the cellulosic material is herbaceous material (including energy crops). In another aspect, the cellulosic material is agricultural residue. In another aspect, the cellulosic material is wood (including forestry residue). In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is wheat straw. In another aspect, the cellulosic material is bagasse. In another aspect, the cellulosic material is corn cob. In another aspect, the cellulosic material is switchgrass. In another aspect, the cellulosic material is corn fiber. In another aspect, the cellulosic material is rice straw. In another aspect, the cellulosic material is miscanthus. In another aspect, the cellulosic material is arundo. In another aspect, the cellulosic material is bamboo. In another aspect, the cellulosic material is orange peel. In another aspect, the cellulosic material is poplar. In another aspect, the cellulosic material is pine. In another aspect, the cellulosic material is aspen. In another aspect, the cellulosic material is fir. In another aspect, the cellulosic material is spruce. In another aspect, the cellulosic material is willow. In another aspect, the cellulosic material is eucalyptus.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

In another aspect, the cellulosic material is an aquatic biomass. As used herein the term "aquatic biomass" means biomass produced in an aquatic environment by a photosynthesis process. The aquatic biomass can be algae; submerged plants; emergent plants; and floating-leaf plants.

The cellulosic material may be used as is or may be subjected to pretreatment (pretreated cellulosic material), using conventional methods known in the art, as described herein.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Dissolved Oxygen Saturation Level: The saturation level of oxygen is determined at the standard partial pressure (0.21 atmosphere) of oxygen. The saturation level at the standard partial pressure of oxygen is dependent on the temperature and solute concentrations. In an embodiment where the temperature during hydrolysis is 50° C., the saturation level would typically be in the range of 5-5.5 mg oxygen per kg slurry, depending on the solute concentrations. Hence, a concentration of dissolved oxygen of 0.5 to 10% of the saturation level at 50° C. corresponds to an amount of dissolved oxygen in a range from 0.025 ppm (0.5×5/100) to 0.55 ppm (10×5.5/100), such as, e.g., 0.05 to 0.165 ppm, and a concentration of dissolved oxygen of 10-70% of the saturation level at 50° C. corresponds to an amount of dissolved oxygen in a range from 0.50 ppm (10×5/100) to 3.85 ppm (70×5.5/100), such as, e.g., 1 to 2 ppm. In an embodiment, oxygen is added in an amount in the range of 0.5 to 5 ppm, such as 0.5 to 4.5 ppm, 0.5 to 4 ppm, 0.5 to 3.5 ppm, 0.5 to 3 ppm, 0.5 to 2.5 ppm, or 0.5 to 2 ppm.

Endoglucanase: The term "endoglucanase" means an endo-1,4-(1,3;1,4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Family 61 glycoside hydrolase: The term "Family 61 glycoside hydrolase" or "Family GH61" or "GH61 polypeptide" means a polypeptide falling into the glycoside hydrolase Family 61 according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. GH61 polypeptides are now classified as lytic polysaccharide monooxygenases (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061) and placed into a new family designated "Auxiliary Activity 9" or "AA9".

GH61 polypeptides enhance hydrolysis/saccharification of a cellulosic material by an enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide for 1-7 days at a suitable temperature, e.g., 50° C., 55° C., or 60° C., compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes NS, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 02/095014) of cellulase protein loading is used as the source of the cellulolytic activity.

GH61 polypeptides enhance the hydrolysis/saccharification of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Feruloyl esterase: The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 micromole of p-nitrophenolate anion per minute at pH 5, 25° C.

Hemicellulose: As used herein, the term "hemicellulose" refers to an oligosaccharide or polysaccharide of biomass material other than cellulose. Hemicellulose is chemically heterogeneous and includes a variety of polymerized sugars, primarily D-pentose sugars, such as xylans, xyloglucans, arabinoxylans, and mannans, in complex heterogeneous branched and linear polysaccharides or oligosaccharides that are bound via hydrogen bonds to the cellulose microfibrils in the plant cell wall, and wherein xylose sugars are usually in the largest amount. Hemicelluloses may be covalently attached to lignin, and usually hydrogen bonded to cellulose, as well as to other hemicelluloses, which help stabilize the cell wall matrix forming a highly complex structure. Hemicellulosic material includes any form of hemicellulose, such as polysaccharides degraded or hydrolyzed to oligosaccharides. It is understood herein that the hemicellulose may be in the form of a component of lignocellulose, a plant cell wall material containing lignin, cellulose, and hemicellulose in a mixed matrix.

Hemicellulolytic enzyme or hemicellulase: The term "hemicellulolytic enzyme" or "hemicellulase" means one or more (several) enzymes that hydrolyze a hemicellulosic material. See, for example, Shallom and Shoham, 2003, Microbial hemicellulases, *Current Opinion In Microbiology* 6(3): 219-228). Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

Host cell: The term "host cell" means any cell type that is susceptible to transformation, transfection, transduction, or the like with a nucleic acid construct or expression vector comprising a polynucleotide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance, or use of a stronger promoter than the promoter naturally associated with the gene encoding the substance). An isolated substance may be present in a fermentation broth.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. The mature polypeptide can be predicted using the SignalP program (Nielsen et al., 1997, *Protein Engineering* 10: 1-6).

Mature polypeptide coding sequence: The term "mature polypeptide coding sequence" is defined herein as a nucleotide sequence that encodes a mature polypeptide having biological activity. The mature polypeptide coding sequence can be predicted using the SignalP program (Nielsen et al., 1997, supra).

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Polypeptide fragment: The term "fragment" means a polypeptide having one or more (e.g., several) amino acids deleted from the amino and/or carboxyl terminus of a mature polypeptide. In one aspect, a fragment contains at least 85% of the amino acid residues, e.g., at least 90% of the amino acid residues or at least 95% of the amino acid residues of the referenced mature polypeptide.

Stringency conditions: For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated Tm using the calculation according to Bolton and McCarthy (1962, *Proc. Natl. Acad. Sci. USA* 48: 1390) in 0.9 M NaCl, 0.09 M Tris HCl pH 7.6, 6 mM EDTA, 0.5% NP 40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated Tm.

Parent Enzyme: The term "parent" means an enzyme to which an alteration is made to produce a variant. The parent may be a naturally occurring (wild-type) polypeptide or a variant thereof.

Pretreated corn stover: The term "PCS" or "Pretreated Corn Stover" means a cellulosic material derived from corn stover by pretreatment (e.g., by heat and dilute sulfuric acid, alkaline pretreatment, or neutral pretreatment).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (several) nucleotides deleted from the 5' and/or 3' end of a mature polypeptide coding sequence; wherein the subsequence encodes a fragment having biological activity.

Variant: The term "variant" means a chitin binding protein comprising an alteration, i.e., a substitution, insertion, and/or deletion of one or more (e.g., several) amino acid residues at one or more positions. A substitution means a replacement of the amino acid occupying a position with a different amino acid; a deletion means removal of the amino acid occupying a position; and an insertion means adding an amino acid adjacent to the amino acid occupying a position.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann et al., 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION

The present invention relates to, inter alia, methods of saccharifying a cellulosic material into sugars, such as fermentable sugars, and converting these sugars into desired products.

The fermentable sugars may be converted to many useful desired substances, e.g., fuel, potable ethanol, and/or fermentation products (e.g., acids, alcohols, ketones, gases, and the like).

The saccharified pretreated cellulosic material may also be sugars that can be used in processes for producing syrups (e.g., High Fructose Corn Syrups (HFCS) and/or plastics (e.g., polyethylene, polystyrene, and polypropylene), polylactic acid (e.g., for producing PET).

Methods of Saccharifying Cellulosic Materials

In one aspect the invention relates to methods of saccharifying a cellulosic material comprising subjecting the cellulosic material to a cellulolytic enzyme composition, a GH61 polypeptide, and a catalase in the presence of dissolved oxygen at a concentration of at least 0.5% of the saturation level.

In the saccharification step, also known as hydrolysis, the cellulosic material, e.g., pretreated cellulosic material, is treated to break down cellulose and/or hemicellulose to fermentable sugars, such as arabinose, cellobiose, galactose, glucose, mannose, xylose, xylulose, and/or soluble oligosaccharides. The saccharification is performed enzymatically by a cellulolytic enzyme composition and a GH61 polypeptide. The enzymes of the compositions can be added simultaneously or sequentially. For instance the GH61 polypeptide may be comprised in the cellulolytic enzyme composition.

Enzymatic saccharification is preferably carried out in a suitable aqueous environment under conditions that can be readily determined by one skilled in the art and in the presence of dissolved oxygen as defined herein. In one aspect, saccharification is performed under conditions suitable for the activity of the enzyme(s), i.e., optimal for the enzyme(s). The saccharification may be carried out as a fed batch or continuous process where the, e.g., pretreated, cellulosic material (substrate) is fed gradually to, for example, an enzyme containing saccharification solution.

According to the invention saccharification may advantageously be performed in stirred-tank reactors, vessels, tanks or fermentors under controlled pH, temperature, and oxygen, and mixing conditions. In an embodiment, the reactor, vessel, tank or fermentor comprises more than 10 m$^3$, such as more than 25 m$^3$, such as more than 50 m$^3$ cellulosic material.

Saccharification may occur for up to 200 hours, e.g., about 12 to about 96 hours, about 16 to about 72 hours, or about 24 to about 48 hours, such as for at least 12 hours, e.g., at least 24 hours, at least 36 hours, at least 48 hours, at least 60 hours, or at least 72 hours.

In an embodiment saccharification is performed at a temperature in the range of about 25° C. to about 75° C., e.g., about 30° C. to about 70° C., about 35° C. to about 65° C., about 40° C. to 60° C., about 45° C. to 55° C., or about 50° C.

In an embodiment saccharification is performed at a pH in the range of about 3.0 to about 9.0, e.g., 3.5 to 6.5, 4.0 to 6.0, 4.5 to 5.5 or about 5.0. In an embodiment, the process of the present invention further comprises adding a base to the tank to maintain the pH in the range of about 3.0 to about 9.0, e.g., 3.5 to 6.5, 4.0 to 6.0, 4.5 to 5.5 or about 5.0. Any base may be used, including but not limited to KOH, NaOH, Ca(OH)$_2$, and NH$_4$OH or a combination thereof. In an embodiment, the base is added in an amount of 25-2,500 mmol base per kg dry cellulosic material, such as 25-1000 mmol/kg, 25-500 mmol/kg, 25-250 mmol/kg, 50-200 mmol/kg. The inventors have determined that less base is required to maintain the pH during saccharification of a cellulosic material with a cellulolytic composition and a GH61 polypeptide in the presence of a catalase compared to the same process with the cellulolytic composition and the GH61 polypeptide but in the absence of a catalase. Thus, the processes of the present invention involving a catalase are less costly and produce less waste in the form of salt. In addition, the processes of the present invention make it easier to recycle spent biomass to the fields, due to the lower content of salts originating from the added base. In an embodiment, the amount of base added during saccharification is reduced by at least 1%, e.g., at least 2.5%, at least 5%, at least 10%, at least 15%, at least 20%, at least 25%, at least 30%, at least 35%, at least 40%, at least 45%, or at least 50%.

The dry solids content during saccharification (e.g., total solids in the cellulosic material) is typically less than about 30 wt. %, 25 wt. %, 20 wt. %, 15 wt. %, 10 wt. %, 7.5 wt. %, 5 wt. %, 2.5 wt. %, 2 wt. %, 1 wt. %, or 0.5 wt. %, such as between 5 and 30 wt. %, such as between 10 and 25 wt. %.

In an embodiment the saccharification is a continuous saccharification in which a cellulosic material and a cellulolytic enzymes composition are added at different intervals throughout the saccharification and the hydrolysate is removed at different intervals throughout the saccharification. The removal of the hydrolysate may occur prior to, simultaneously with, or after the addition of the cellulosic material and the cellulolytic enzymes composition.

In an embodiment of the invention the dissolved oxygen concentration during saccharification is in the range of about 0.5-10% of the saturation level, such as 0.5-5%, such as 0.5-4%, such as 0.5-3%, such as 0.5-2%, such as 1-5%, such as 1-4%, such as 1-3%, such as 1-2%. In a preferred embodiment the dissolved oxygen concentration is maintained in the range of about 0.5-10% of the saturation level, such as 0.5-5%, such as 0.5-4%, such as 0.5-3%, such as 0.5-2%, such as 1-5%, such as 1-4%, such as 1-3%, such as 1-2% during at least 25%, such as at least 50%, such as at least 75% of the saccharification period.

In an embodiment of the invention the dissolved oxygen concentration during saccharification is in the range of greater than 10% up to 90% of the saturation level, such as greater than 10% up to 80%, greater than 10% up to 70%, greater than 10% up to 60%, greater than 10% up to 50%, greater than 10% up to 40%, greater than 10% up to 30%, and greater than 10% up to 20%. In a preferred embodiment the dissolved oxygen concentration is maintained at a concentration of greater than 10% up to 90% of the saturation level, such as greater than 10% up to 80%, greater than 10% up to 70%, greater than 10% up to 60%, greater than 10% up to 50%, greater than 10% up to 40%, greater than 10% up to 30%, and greater than 10% up to 20% during at least 25%, such as at least 50% or at least 75% of the saccharification period.

Oxygen is added to the vessel in order to achieve the desired concentration of dissolved oxygen during saccharification. Maintaining the dissolved oxygen level within a desired range can be accomplished by aeration of the vessel, tank or the like by adding compressed air through a diffuser or sparger, or by other known methods of aeration. The aeration rate can be controlled on the basis of feedback from a dissolved oxygen sensor placed in the vessel/tank, or the system can run at a constant rate without feedback control. In the case of a hydrolysis train consisting of a plurality of vessels/tanks connected in series, aeration can be implemented in one or more or all of the vessels/tanks. Oxygen aeration systems are well known in the art. According to the invention any suitable aeration system may be used. Commercial aeration systems are designed by, e.g., Chemineer, Derby, England, and build by, e.g., Paul Mueller Company, MO, USA.

Methods of Producing Fermentation Products from Cellulosic Materials

In another aspect the invention relates methods of producing a fermentation product, comprising:

(a) subjecting a cellulosic material to a cellulolytic enzyme composition, a GH61 polypeptide, and a catalase in the presence of dissolved oxygen at a concentration of at least 0.5% of the saturation level;

(b) fermenting the saccharified cellulosic material with one or more fermenting microorganisms; and (c) optionally recovering the fermentation product from (b).

During fermentation, the sugars produced in the saccharification process are converted into a desired product. Fermentable sugars may be converted to many useful desired substances, e.g., fuel, potable ethanol, and/or fermentation products (e.g., acids, alcohols, ketones, gases, and the like). Other sugars may be used in processes for producing syrups (e.g., High Fructose Corn Syrups (HFCS) and/or plastics (e.g., polyethylene, polystyrene, and polypropylene), polylactic acid (e.g., for producing PET) and more.

Saccharification and fermentation may be carried out separately or simultaneously. This includes, but is not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC). SHF uses separate steps to first enzymatically saccharify (hydrolyze) cellulosic material to fermentable sugars, e.g., glucose, cellobiose, cellotriose, and pentose sugars, and then ferment the fermentable sugars to ethanol. In SSF, the enzymatic saccharification of cellulosic materials and the fermentation of sugars to, e.g., ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan and Himmel, 1999, Enzymes, energy and the environment: A strategic perspective on the U.S. Department of Energy's research and development activities for bioethanol, *Biotechnol. Prog.* 15: 817-827). HHF involves a separate saccharification (hydrolysis) step, and in addition a simultaneous saccharification and fermentation step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd et al., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used for practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza et al., 2003, Optimal control in fed-batch reactor for the cellobiose hydrolysis, *Acta Scientiarum. Technology* 25: 33-38; Gusakov and Sinitsyn, 1985, Kinetics of the enzymatic hydrolysis of cellulose: 1. A mathematical model for a batch reactor process, *Enz. Microb. Technol.* 7: 346-352), an attrition reactor (Ryu and Lee, 1983, Bioconversion of waste cellulose by using an attrition bioreactor, *Biotechnol. Bioeng.* 25: 53-65), or a reactor with intensive stirring induced by an electromagnetic field (Gusakov et al., 1996, Enhancement of enzymatic cellulose saccharification using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Cellulosic Material.

The cellulosic material may be any biomass material. In a preferred embodiment the cellulosic material has been pretreated, e.g., by chemical and/or physical pretreatment, such as by dilute acid and/or steam explosion pretreatment. Examples of suitable pretreatments can be found in the "Pretreatment"-section below. The cellulosic material may be pretreated corn stover (PCS), such as dilute acid pretreated corn stover. The cellulosic material may also be unwashed, such as unwashed pretreated corn stover (uwPCS).

Pretreatment.

The cellulosic material may be pretreated, e.g., by a chemical pretreatment, a physical pretreatment, or a chemical pretreatment and a physical pretreatment, as described below. In one aspect, the pretreated cellulosic material is pretreated by a chemical pretreatment. In another aspect, the pretreated cellulosic material is pretreated by physical pretreatment. In another aspect, the pretreated cellulosic material is pretreated by a chemical pretreatment and a physical pretreatment. In some aspects, the pretreated cellulosic material is pretreated corn stover (PCS).

Any suitable pretreatment process known in the art can be used to disrupt plant cell wall components of cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of cellulosic material to fermentable sugars (even in absence of enzymes).

Steam Pretreatment.

In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment may be performed at 140-230° C., e.g., 160-200° C., or 170-190° C., where the optimal temperature range depends on any addition of a chemical catalyst. The residence time for the steam pretreatment may be 1-15 minutes, e.g., 3-12 minutes, or 4-10 minutes, where the optimal residence time depends on temperature range and any addition of a chemical catalyst. Steam pretreatment allows for relatively high solids loadings, so that cellulosic material is generally only moist during the pretreatment. Steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to hemicellulose monosaccharides and hemicellulose oligosaccharides, which become more solubilized. Lignin is removed to only a limited extent. The resulting liquor primarily contains dissolved hemicellulosic material (e.g., hemicellulose monosaccharides and hemicellulose oligosaccharides), whereas the remaining solids primarily consists of cellulosic material.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment.

The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* 105-108: 69-85, and Mosier et al., 2005, *Bioresource Technology* 96: 673-686, and U.S. Published Application No. 2002/0164730.

In one aspect, the chemical pretreatment is carried out as an acid treatment, such as a continuous dilute and/or mild acid treatment. The acid is may be sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range of 0.01 to 20 wt. % acid, preferably 0.05 to 10 wt. % acid, more preferably 0.1 to 5 wt. % acid, and most preferably 0.2 to 2.0 wt. % acid. The acid is contacted with biomass material and held at a temperature in the range of preferably 160-220° C., and more preferably 165-195° C., for periods ranging from seconds to minutes, e.g., 1 second to 60 minutes.

In another aspect, pretreatment is carried out as an ammonia fiber explosion step (AFEX pretreatment step).

In another aspect, pretreatment takes place in an aqueous slurry. In one aspect, cellulosic material is present during pretreatment in amounts preferably between 10-80 wt. %, e.g., between 20-70 wt. %, or between 30-60 wt. %, such as around 50 wt. %. The pretreated cellulosic material can be unwashed or washed using any method known in the art, e.g., washed with water.

Mechanical Pretreatment or Physical Pretreatment.

The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, more preferably about 150 to about 250 psi. In another aspect, high temperature means temperatures in the range of about 100 to about 300° C., preferably about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment:

The term "biological pretreatment" refers to any biological pretreatment that promotes the separation and/or release of cellulose, hemicellulose, and/or lignin from biomass material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, Enz. Microb. Tech. 18: 312-331; and Vallander and Eriksson, 1990, Production of ethanol from lignocellulosic materials: State of the art, *Adv. Biochem. Eng./Biotechnol.* 42: 63-95).

Fermentation.

The fermentable sugars obtained from the saccharifying cellulosic material in accordance with the invention can be fermented by one or more (several) fermenting microorganisms capable of fermenting the sugars (e.g., glucose, xylose) directly or indirectly into a desired fermentation product (e.g., ethanol).

"Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the enzymatic saccharification, are fermented to a product, e.g., ethanol, by a fermenting organism, such as yeast. Saccharification and fermentation can be separate or simultaneous, as described herein.

Any suitable cellulosic material saccharified according to the invention can be used in the fermentation step in practicing the present invention. The material is generally selected based on the desired fermentation product, i.e., the substance to be obtained from the fermentation, and the process employed.

The term "fermentation medium" is understood herein to refer to a medium before the fermenting microorganism(s) is(are) added, such as, a medium resulting from saccharification, as well as a medium used in, e.g., a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of *Saccharomyces* spp., preferably *Saccharomyces cerevisiae*.

Examples of fermenting organisms that can ferment $C_5$ sugars include bacterial and fungal organisms, such as yeast. Preferred $C_5$ fermenting yeast include strains of *Pichia*, preferably *Pichia stipitis*, such as *Pichia stipitis* CBS 5773; strains of *Candida*, preferably *Candida boidinii, Candida brassicae, Candida sheatae, Candida diddensii, Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. marxianus, K. lactis, K. thermotolerans*, and *K. fragilis*; *Schizosaccharomyces*, such as *S. pombe*; *E. coli*, especially *E. coli* strains that have been genetically modified to improve the yield of ethanol; *Clostridium*, such as *Clostridium acetobutylicum, Chlostridium thermocellum*, and *Chlostridium phytofermentans*; *Geobacillus* sp.; *Thermoanaerobacter*, such as *Thermoanaerobacter saccharolyticum*; and *Bacillus*, such as *Bacillus coagulans*; *Candida*, such as *C. sonorensis, C. methanosorbosa, C. diddensiae, C. parapsilosis, C. naedodendra, C. blankii C. entomophilia, C. brassicae, C. pseudotropicalis, C. boidinii, C. utilis*, and *C. scehatae*; *Klebsiella*, such as *K. oxytoca*.

In one aspect, the yeast is a *Saccharomyces* spp. In another aspect, the yeast is *Saccharomyces cerevisiae*. In another aspect, the yeast is *Saccharomyces distaticus*. In another aspect, the yeast is *Saccharomyces uvarum*. In another aspect, the yeast is a *Kluyveromyces*. In another aspect, the yeast is *Kluyveromyces marxianus*. In another aspect, the yeast is *Kluyveromyces fragilis*. In another aspect, the yeast is a *Candida*. In another aspect, the yeast is *Candida boidinii*. In another aspect, the yeast is *Candida brassicae*. In another aspect, the yeast is *Candida diddensii*. In another aspect, the yeast is *Candida pseudotropicalis*. In another aspect, the yeast is *Candida utilis*. In another aspect, the yeast is a *Clavispora*. In another aspect, the yeast is *Clavispora lusitaniae*. In another aspect, the yeast is *Clavispora opuntiae*. In another aspect, the yeast is a *Pachysolen*. In another aspect, the yeast is *Pachysolen tannophilus*. In another aspect, the yeast is a *Pichia*. In another aspect, the yeast is a *Pichia stipitis*. In another aspect, the yeast is a *Bretannomyces*. In another aspect, the yeast is *Bretannomyces clausenii* (Philippidis, 1996, supra).

Bacteria that can efficiently ferment hexose and pentose to ethanol include, for example, *Zymomonas mobilis, Clostridium acetobutylicum, Clostridium thermocellum, Clostridium phytofermentans, Geobacillus* sp., *Thermoanaerobacter saccharolyticum*, and *Bacillus coagulans* (Philippidis, 1996, supra).

In one aspect, the bacterium is a *Zymomonas*. In one aspect, the bacterium is *Zymomonas mobilis*. In another aspect, the bacterium is a *Clostridium*. In another aspect, the bacterium is *Clostridium acetobutylicum*. In another aspect, the bacterium is *Clostridium phytofermentan*. In another aspect, the bacterium is *Clostridium thermocellum*. In another aspect, the bacterium is *Geobacillus* sp. In another aspect, the bacterium is *Thermoanaerobacter saccharolyticum*. In another aspect, the bacterium is *Bacillus coagulans*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In one aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 03/062430, xylose isomerase).

In one aspect, the genetically modified fermenting microorganism is *Saccharomyces cerevisiae*. In another aspect, the genetically modified fermenting microorganism is *Zymomonas mobilis*. In another aspect, the genetically modified fermenting microorganism is *Escherichia coli*. In another aspect, the genetically modified fermenting microorganism is *Klebsiella oxytoca*. In another aspect, the genetically modified fermenting microorganism is *Kluyveromyces* sp.

It is well known in the art that the organisms described above can also be used to produce other substances, as described herein.

The fermenting microorganism is typically added to saccharified pretreated cellulosic material and the fermentation may be performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In one aspect, the yeast and/or another microorganism, is applied to the saccharified pretreated cellulosic material and then fermentation is performed for about 12 hours to about 96 hours, such as 24-60 hours. In one aspect, the temperature is between about 20° C. to about 60° C., e.g., about 25° C. to about 50° C., or about 32° C. to about 50° C., and the pH is generally from about pH 3 to about pH 7, e.g., around pH 4-7, such as about pH 5.

However, some fermenting organisms, e.g., bacteria, have higher fermentation temperature optima. Yeast or another microorganism is preferably applied in amounts of approximately $10^5$ to $10^{12}$, e.g., from approximately $10^7$ to $10^{10}$, especially approximately $2 \times 10^8$ viable cell count per mL of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation, the fermented slurry may be distilled to extract the ethanol. The ethanol obtained according to a method of the invention can be used as, e.g., fuel ethanol, drinking ethanol, i.e., potable neutral spirits, or industrial ethanol.

A fermentation stimulator can be used in combination with any of the methods described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

The fermentation product can be any substance derived from fermentation. The fermentation product can, without limitation, be an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); and a gas (e.g., methane, hydrogen ($H_2$), carbon dioxide ($CO_2$), and carbon monoxide (CO)). The fermentation product can also be protein as a high value product.

In one aspect, the fermentation product is an alcohol. It will be understood that the term "alcohol" encompasses a substance that contains one or more hydroxyl moieties. In one aspect, the alcohol is arabinitol. In another aspect, the alcohol is butanol. In another aspect, the alcohol is ethanol. In another aspect, the alcohol is glycerol. In another aspect, the alcohol is methanol. In another aspect, the alcohol is 1,3-propanediol. In another aspect, the alcohol is sorbitol. In another aspect, the alcohol is xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another aspect, the fermentation product is an organic acid. In one aspect, the organic acid is acetic acid. In another aspect, the organic acid is acetonic acid. In another aspect, the organic acid is adipic acid. In another aspect, the organic acid is ascorbic acid. In another aspect, the organic acid is citric acid. In another aspect, the organic acid is 2,5-diketo-D-gluconic acid. In another aspect, the organic acid is formic acid. In another aspect, the organic acid is fumaric acid. In another aspect, the organic acid is glucaric acid. In another aspect, the organic acid is gluconic acid. In another aspect, the organic acid is glucuronic acid. In another aspect, the organic acid is glutaric acid. In another aspect, the organic acid is 3-hydroxypropionic acid. In another aspect, the organic acid is itaconic acid. In another aspect, the organic acid is lactic acid. In another aspect, the organic acid is malic acid. In another aspect, the organic acid is malonic acid. In another aspect, the organic acid is oxalic acid. In another aspect, the organic acid is propionic acid. In another aspect, the organic acid is succinic acid. In another aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

In another aspect, the fermentation product is a ketone. It will be understood that the term "ketone" encompasses a substance that contains one or more ketone moieties. In another aspect, the ketone is acetone. See, for example, Qureshi and Blaschek, 2003, supra.

In another aspect, the fermentation product is an amino acid. In one aspect, the amino acid is aspartic acid. In another aspect, the amino acid is glutamic acid. In another aspect, the amino acid is glycine. In another aspect, the amino acid is lysine. In another aspect, the amino acid is serine. In another aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another aspect, the fermentation product is an alkane. The alkane can be an unbranched or a branched alkane. In one aspect, the alkane is pentane. In another aspect, the alkane is hexane. In another aspect, the alkane is heptane. In another aspect, the alkane is octane. In another aspect, the alkane is nonane. In another aspect, the alkane is decane. In another aspect, the alkane is undecane. In another aspect, the alkane is dodecane.

In another aspect, the fermentation product is a cycloalkane. In one aspect, the cycloalkane is cyclopentane. In another aspect, the cycoalkane is cyclohexane. In another aspect, the cycloalkane is cycloheptane. In another aspect, the cycloalkane is cyclooctane.

In another aspect, the fermentation product is an alkene. The alkene can be an unbranched or a branched alkene. In one aspect, the alkene is pentene. In another aspect, the alkene is hexene. In another aspect, the alkene is heptene. In another aspect, the alkene is octene.

In one aspect, the fermentation product is isoprene. In another aspect, the fermentation product is polyketide.

In another aspect, the fermentation product is a gas. In one aspect, the gas is methane. In another aspect, the gas is $H_2$. In another aspect, the gas is $CO_2$. In another aspect, the gas is CO. See, for example, Kataoka et al., 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy* 13(1-2): 83-114.

Recovery.

The fermentation product(s) may optionally be recovered from the fermentation medium using any method known in the art including, but not limited to, chromatography, electrophoretic procedures, differential solubility, distillation, or extraction. For example, alcohol is separated from the fermented sugar cane trash and purified by conventional methods of distillation. Ethanol with a purity of up to about 96 vol. % can be obtained, which can be used as, for example, fuel ethanol, drinking ethanol, i.e., potable neutral spirits, or industrial ethanol.

Enzymes

The enzyme(s) and polypeptides described below are to be used in an "effective amount" in processes of the present invention. Below should be read in context of the enzyme disclosure in the "Definitions"-section above.

Cellulolytic Enzyme Compositions Used for Saccharification

The cellulolytic enzyme compositions can comprise any protein useful in degrading the cellulosic material. The cellulolytic enzyme composition used for saccharification may be of any origin, such as microbial origin, such as eukaryotic origin, such as fungal origin, e.g., filamentous fungal origin.

In one aspect, the cellulolytic enzyme composition comprises or further comprises one or more (e.g., several)

proteins selected from the group consisting of a cellulase, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is a catalase, a laccase, or a peroxidase.

In another aspect, the cellulolytic enzyme composition comprises one or more (e.g., several) cellulolytic enzymes. In another aspect, the cellulolytic enzyme composition comprises or further comprises one or more (e.g., several) hemicellulolytic enzymes. In another aspect, the cellulolytic enzyme composition comprises one or more (e.g., several) cellulolytic enzymes and one or more (e.g., several) hemicellulolytic enzymes. In another aspect, the cellulolytic enzyme composition comprises an endoglucanase. In another aspect, the cellulolytic enzyme composition comprises a cellobiohydrolase. In another aspect, the cellulolytic enzyme composition comprises a beta-glucosidase. In another aspect, the cellulolytic enzyme composition comprises an endoglucanase and a cellobiohydrolase. In another aspect, the cellulolytic enzyme composition comprises an endoglucanase and a cellobiohydrolase I, a cellobiohydrolase II, or a combination of a cellobiohydrolase I and a cellobiohydrolase II. In another aspect, the cellulolytic enzyme composition comprises an endoglucanase and a beta-glucosidase. In another aspect, the cellulolytic enzyme composition comprises a beta-glucosidase and a cellobiohydrolase. In another aspect, the cellulolytic enzyme composition comprises a beta-glucosidase and a cellobiohydrolase I, a cellobiohydrolase II, or a combination of a cellobiohydrolase I and a cellobiohydrolase II. In another aspect, the cellulolytic enzyme composition comprises an endoglucanase, a beta-glucosidase, and a cellobiohydrolase. In another aspect, the cellulolytic enzyme composition comprises an endoglucanase, a beta-glucosidase, and a cellobiohydrolase I, a cellobiohydrolase II, or a combination of a cellobiohydrolase I and a cellobiohydrolase II.

In another aspect, the cellulolytic enzyme composition comprises an acetylmannan esterase. In another aspect, the cellulolytic enzyme composition comprises an acetylxylan esterase. In another aspect, the cellulolytic enzyme composition comprises an arabinanase (e.g., alpha-L-arabinanase). In another aspect, the cellulolytic enzyme composition comprises an arabinofuranosidase (e.g., alpha-L-arabinofuranosidase). In another aspect, the cellulolytic enzyme composition comprises a coumaric acid esterase. In another aspect, the enzyme composition comprises a feruloyl esterase. In another aspect, the cellulolytic enzyme composition comprises a galactosidase (e.g., alpha-galactosidase and/or beta-galactosidase). In another aspect, the cellulolytic enzyme composition comprises a glucuronidase (e.g., alpha-D-glucuronidase). In another aspect, the cellulolytic enzyme composition comprises a glucuronoyl esterase. In another aspect, the cellulolytic enzyme composition comprises a mannanase. In another aspect, the cellulolytic enzyme composition comprises a mannosidase (e.g., beta-mannosidase). In another aspect, the cellulolytic enzyme composition comprises a xylanase. In an embodiment, the xylanase is a Family 10 xylanase. In another embodiment, the xylanase is a Family 11 xylanase. In another aspect, the cellulolytic enzyme composition comprises a xylosidase (e.g., beta-xylosidase).

In another aspect, the cellulolytic enzyme composition comprises a CIP. In another aspect, the cellulolytic enzyme composition comprises an esterase. In another aspect, the cellulolytic enzyme composition comprises an expansin. In another aspect, the cellulolytic enzyme composition comprises a ligninolytic enzyme. In an embodiment, the ligninolytic enzyme is a manganese peroxidase. In another embodiment, the ligninolytic enzyme is a lignin peroxidase. In another embodiment, the ligninolytic enzyme is a $H_2O_2$-producing enzyme. In another aspect, the cellulolytic enzyme composition comprises a pectinase. In another aspect, the cellulolytic enzyme composition comprises an oxidoreductase. In another embodiment, the oxidoreductase is a laccase. In another embodiment, the oxidoreductase is a peroxidase. In another aspect, the enzyme composition comprises a protease. In another aspect, the enzyme composition comprises a swollenin.

In an embodiment the cellulolytic enzyme composition is derived or isolated from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme composition is derived or isolated from a strain of *Trichoderma reesei*.

Examples of *Trichoderma reseei* cellulolytic enzyme compositions with recombinantly produced GH61 polypeptide are described in WO 2008/151079 (Novozymes) and WO 2013/028928 (Novozymes) which are both hereby incorporated by reference. Examples of suitable GH61 polypeptides can be found in the "GH61 polypeptide"-section below.

The cellulolytic enzyme composition may further comprise one or more enzymes selected from the group consisting of: esterases, expansins, hemicellulases, laccases, ligninolytic enzymes, pectinases, peroxidases, proteases, superoxide dismutases, and swollenins.

The optimum amount of the cellulolytic enzyme composition depends on several factors including, but not limited to, the mixture of component enzymes, the cellulosic material, the concentration of the cellulosic material, the pretreatment(s) of the cellulosic material, temperature, time, pH, and inclusion of fermenting organism (e.g., yeast).

The cellulolytic enzyme composition may be added in an amount of about 0.01 to about 50.0 mg, e.g., about 1 to about 25 mg, such as about 2-10 mg, such as about 4 to about 8 mg protein per g/DS of the cellulosic material.

Beta-Glucosidases

The cellulolytic enzyme composition used according to the invention may in one embodiment comprise one or more beta-glucosidases. The beta-glucosidase may be of any origin, such as microbial origin, such as eukaryotic origin, such as fungal origin, e.g., filamentous origin.

In one embodiment the beta-glucosidase is from a strain of *Aspergillus*, such as *Aspergillus oryzae*, such as the one disclosed in WO 02/095014 or the fusion protein having beta-glucosidase activity disclosed in WO 2008/057637 (see e.g., Examples 10-15), or *Aspergillus fumigatus*, such as the one disclosed as SEQ ID NO: 2 in WO 2005/047499 or SEQ ID NO: 5 herein or an *Aspergillus fumigatus* beta-glucosidase variant, such as one disclosed in WO 2012/044915, such as one with the following substitutions: F100D, S283G, N456E, F512Y (using SEQ ID NO: 5 herein for numbering).

In another embodiment the beta-glucosidase is derived from a strain of *Penicillium*, such as a strain of the *Penicillium brasilianum* disclosed as SEQ ID NO: 2 in WO 2007/019442, or a strain of *Trichoderma*, such as a strain of *Trichoderma reesei*.

In an embodiment the beta-glucosidase is an *Aspergillus fumigatus* beta-glucosidase or homolog thereof selected from the group consisting of:

(i) a beta-glucosidase comprising the mature polypeptide of SEQ ID NO: 2 in WO 2005/047499 or SEQ ID NO: 5 herein;

(ii) a beta-glucosidase comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 2 in WO 2005/047499 or SEQ ID NO: 5 herein;

(iii) a beta-glucosidase encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 1 in WO 2005/047499; and (iv) a beta-glucosidase encoded by a polynucleotide that hybridizes under medium, high stringency conditions, or very high stringency conditions, with the mature polypeptide coding sequence of SEQ ID NO: 1 in WO 2005/047499 or the full-length complement thereof.

In an embodiment the beta-glucosidase is a variant comprising a substitution at one or more (several) positions corresponding to positions 100, 283, 456, and 512 of the mature polypeptide of SEQ ID NO: 2 in WO 2005/047499 or SEQ ID NO: 5 herein, wherein the variant has beta-glucosidase activity.

In an embodiment the parent beta-glucosidase of the variant is (a) a polypeptide comprising the mature polypeptide of SEQ ID NO: 2 in WO 2005/047499 or SEQ ID NO: 5 herein; (b) a polypeptide having at least 80% sequence identity to the mature polypeptide of SEQ ID NO: 5 herein; (c) a polypeptide encoded by a polynucleotide that hybridizes under low, medium, high or very high stringency conditions with (i) the mature polypeptide coding sequence of SEQ ID NO: 1 in WO 2005/047499 (hereby incorporated by reference), (ii) the cDNA sequence contained in the mature polypeptide coding sequence of SEQ ID NO: 5, or (iii) the full-length complementary strand of (i) or (ii); (d) a polypeptide encoded by a polynucleotide having at least 80% identity to the mature polypeptide coding sequence of SEQ ID NO: 1 in WO 2005/047499 or the cDNA sequence thereof; or (e) a fragment of the mature polypeptide of SEQ ID NO: 2 in WO 2005/047499, which has beta-glucosidase activity.

In an embodiment the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

In an embodiment the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 2 in WO 2005/047499 or SEQ ID NO: 5 herein.

In an embodiment the number of substitutions is between 1 and 4, such as 1, 2, 3, or 4 substitutions.

In an embodiment the variant comprises a substitution at a position corresponding to position 100, a substitution at a position corresponding to position 283, a substitution at a position corresponding to position 456, and/or a substitution at a position corresponding to position 512.

In an embodiment the beta-glucosidase variant comprises the following substitutions: Phe100Asp, Ser283Gly, Asn456Glu, Phe512Tyr in SEQ ID NO: 2 in WO 2005/047499 or SEQ ID NO: 5 herein.

Endoglucanases

The cellulolytic enzyme composition used according to the invention comprises one or more endoglucoanases. The endoglucanase may be of any origin, such as microbial origin, such as eukaryotic origin, such as fungal origin, e.g., filamentous origin.

In an embodiment the endoglucanase(s) may be from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the endoglucoamase is derived from a strain of *Trichoderma reesei*.

Examples of fungal endoglucanases that can be used according to the present invention include, but are not limited to, a *Trichoderma reesei* endoglucanase I (Penttila et al., 1986, *Gene* 45: 253-263; *Trichoderma reesei* Cel7B endoglucanase I; GENBANK™ accession no. M15665; *Trichoderma reesei* endoglucanase II (Saloheimo, et al., 1988, *Gene* 63:11-22; *Trichoderma reesei* Cel5A endoglucanase II; GENBANK™ accession no. M19373; *Trichoderma reesei* endoglucanase III (Okada et al., 1988, *Appl. Environ. Microbiol.* 64: 555-563; GENBANK™ accession no. AB003694; *Trichoderma reesei* endoglucanase V (Saloheimo et al., 1994, Molecular Microbiology 13: 219-228; GENBANK™ accession no. Z33381; *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase; *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase; GENBANK™ accession no. M15665.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Cellobiohydrolase I

The cellulolytic composition used according to the invention may comprise one or more CBH I (cellobiohydrolase I). The cellobiohydrolase I may be of any origin, such as microbial origin, such as eukaryotic origin, such as fungal origin, e.g., filamentous origin.

In one embodiment the cellulolytic enzyme composition comprises a cellobiohydrolase I (CBHI), such as one derived or isolated from a strain of *Aspergillus*, such as a strain of *Aspergillus fumigatus*, such as the Cel7A CBH I disclosed in SEQ ID NO: 6 in WO 2011/057140 or SEQ ID NO: 6 herein, or a strain of *Trichoderma*, such as a strain of *Trichoderma reesei*.

In an embodiment the *Aspergillus fumigatus* cellobiohydrolase I (CBH I) or homolog thereof is selected from the group consisting of:

(i) a cellobiohydrolase I comprising the mature polypeptide of SEQ ID NO: 6 herein;

(ii) a cellobiohydrolase I comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 6 herein;

(iii) a cellobiohydrolase I encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 5 in WO 2011/057140 (hereby incorporated by reference); and (iv) a cellobiohydrolase I encoded by a polynucleotide that hybridizes under low, medium, high, or very high stringency conditions, with the mature polypeptide coding sequence of SEQ ID NO: 5 in WO 2011/057140 or the full-length complement thereof.

Cellobiohydrolase II

The cellulolytic composition used according to the invention may comprise one or more CBH II (cellobiohydrolase II). The cellobiohydrolase II may be of any origin, such as microbial origin, such as eukaryotic origin, such as fungal origin, e.g., filamentous origin.

In one embodiment the cellobiohydrolase II (CBHII), such as one derived from a strain of *Aspergillus*, such as a strain of *Aspergillus fumigatus*, such as the one in SEQ ID NO: 7 herein or a strain of *Trichoderma*, such as *Trichoderma reesei*, or a strain of *Thielavia*, such as a strain of *Thielavia terrestris*, such as cellobiohydrolase II CEL6A from *Thielavia terrestris*.

In an embodiment the *Aspergillus fumigatus* cellobiohydrolase II or homolog thereof is selected from the group consisting of:

(i) a cellobiohydrolase II comprising the mature polypeptide of SEQ ID NO: 4;

(ii) a cellobiohydrolase II comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 7 herein;

(iii) a cellobiohydrolase II encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 3 in WO 2013/028928 (hereby incorporated by reference); and (iv) a cellobiohydrolase II encoded by a polynucleotide that hybridizes under low, medium, or high stringency conditions, e.g., very high stringency conditions, with the mature polypeptide coding sequence of SEQ ID NO: 3 in WO 2013/028928 or the full-length complement thereof.

GH61 Polypeptides

A GH61 polypeptide is according to the invention present during saccharification together with a cellulolytic enzyme composition. The GH61 polypeptide may be of any origin, such as microbial origin, such as eukaryotic origin, such as fungal origin, e.g., filamentous origin.

The GH61 polypeptide may be added separately, simultaneously with or as part of the cellulolytic enzyme composition.

The GH61 polypeptide may be native or foreign to the strain from which the cellulolytic enzyme composition is derived or isolated, such as a strain of *Trichoderma reesei*, *Humicola insolens*, *Talaromyces emersonii*, or *Chrysosporium lucknowense* (*Myceliophthora thermophila*). In an embodiment the GH61 polypeptide is a recombinant GH61 polypeptide. In an embodiment the GH61 polypeptide is not of the same origin as the cellulolytic enzyme composition's host cell, e.g., not of *Trichoderma* origin, such as not of *Trichoderma reesei* origin. In an embodiment the GH61 polypeptide is produced recombinantly as part of the cellulolytic enzyme composition, e.g., produced by the *Trichoderma reesei* host cell producing the cellulolytic enzyme composition.

In one embodiment the GH61 polypeptide is derived or isolated from *Thermoascus*, such as a strain of *Thermoascus aurantiacus*, such as the one described in WO 2005/074656 as SEQ ID NO: 2 and SEQ ID NO: 1 herein; or derived or isolated from *Thielavia*, such as a strain of *Thielavia terrestris*, such as the one described in WO 2005/074647 as SEQ ID NO: 8 or SEQ ID NO: 4 herein; or derived or isolated from a strain of *Aspergillus*, such as a strain of *Aspergillus fumigatus*, such as the one described in WO 2010/138754 as SEQ ID NO: 2 or SEQ ID NO: 3 herein; or derived or isolated from a strain of *Penicillium*, such as a strain of *Penicillium emersonii*, such as the one disclosed as SEQ ID NO: 2 in WO 2011/041397 or SEQ ID NO: 2 herein.

In an embodiment the *Penicillium* sp. GH61 polypeptide or homolog thereof is selected from the group consisting of:

(i) a GH61 polypeptide comprising the mature polypeptide of SEQ ID NO: 8 herein;

(ii) a GH61 polypeptide comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 8 herein;

(iii) a GH61 polypeptide encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 1 in WO 2011/041397 (hereby incorporated by reference); and (iv) a GH61 polypeptide encoded by a polynucleotide that hybridizes under low, medium, high, or very high stringency conditions, with the mature polypeptide coding sequence of SEQ ID NO: 1 in WO 2011/041397 or the full-length complement thereof.

In an embodiment the polypeptide or homolog thereof is selected from the group consisting of a GH61 polypeptide comprising the mature polypeptide of SEQ ID NO: 2 in WO 2005/074656; SEQ ID NO: 8 in WO 2005/074647; SEQ ID NO: 2 in WO 2010/138754; or a GH61 polypeptide comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 2 in WO 2005/074656; SEQ ID NO: 8 in WO 2005/074647; or SEQ ID NO: 2 in WO 2010/138754 (all references and sequences hereby incorporated by reference).

In an embodiment the GH61 polypeptide constitutes from 0.1-25%, such as 0.5-20%, 0.5-15%, 0.5-10%, or 0.5-7% of the cellulolytic enzyme composition. In an embodiment the amount of GH61 polypeptide to cellulolytic enzyme composition is about 1 g to about 1000 g, such as about 1 g to about 200 g, about 1 g to about 100 g, about 1 g to about 50 g, about 1 g to about 20 g, about 1 g to about 15 g, about 1 g to about 10 g, about 1 g to about 7 g, or about 1 g to about 4 g per g of cellulolytic enzyme composition.

Specific Cellulosic Enzyme Compositions Comprising a GH61 Polypeptide

The following is a list of a number of cellulolytic enzyme compositions comprising a GH61 polypeptide for use in the present invention.

In an embodiment the cellulolytic enzyme composition comprises a *Trichoderma reesei* cellulolytic enzyme composition, further comprising a *Thermoascus aurantiacus* GH61A polypeptide (WO 2005/074656 and SEQ ID NO: 1 herein) and an *Aspergillus oryzae* beta-glucosidase fusion protein (see WO 2008/057637—Examples 10-15).

In another embodiment the cellulolytic enzyme composition comprises a *Trichoderma reesei* cellulolytic enzyme composition, further comprising a *Thermoascus aurantiacus* GH61A polypeptide (SEQ ID NO: 2 in WO 2005/074656 or SEQ ID NO: 1 herein) and an *Aspergillus fumigatus* beta-glucosidase (SEQ ID NO: 2 of WO 2005/047499 or SEQ ID NO: 5 herein).

In another embodiment the cellulolytic composition comprises a *Trichoderma reesei* cellulolytic enzyme composition, further comprising a *Penicillium emersonii* GH61A polypeptide disclosed as SEQ ID NO: 2 in WO 2011/041397 or SEQ ID NO: 2 herein, an *Aspergillus fumigatus* beta-glucosidase (SEQ ID NO: 2 of WO 2005/047499 or SEQ ID NO: 5 herein) or a variant thereof with the following substitutions: F100D, S283G, N456E, F512Y (using SEQ ID NO: 5 herein for numbering)(disclosed in WO 2012/044915).

Formulation of Cellulolytic Enzyme Compositions

A cellulolytic enzyme composition used according to the invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes.

The cellulolytic enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Commercial Cellulolytic Enzyme Compositions

The cellulolytic enzyme compositions used in accordance with the methods of the invention may be a commercial cellulolytic enzyme composition. Examples of commercial cellulolytic enzyme composition suitable for use according to the present invention include, for example, CELLIC™ CTec (Novozymes NS), CELLIC™ CTec2 (Novozymes NS), CELLIC™ CTec3 (Novozymes NS), CELLUCLAST™ (Novozymes NS), NOVOZYM™ 188 (Novozymes NS), CELLUZYME™ (Novozymes NS), CEREFLO™ (Novozymes NS), and ULTRAFLO™ (Novozymes NS), ACCELERASE™ (DuPont), ACCELERASE™ 1000; ACCELERASE™ 1500; ACCELERASE™ TRIO; ACCELERASE™ DUET (DuPont); LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). A commercial cellulolytic enzyme composition may be added in an amount of about 0.001 to about 5.0 wt. % of solids, more preferably from about 0.025 to about 4.0 wt. % of solids, and most preferably from about 0.005 to about 2.0 wt. % of dry solids (DS).

Catalases

The catalase may be any catalase useful in the processes of the present invention. The catalase may include, but is not limited to, an E.C. 1.11.1.6 or E.C. 1.11.1.21 catalase.

Examples of useful catalases include, but are not limited to, catalases from *Alcaligenes aquamarinus* (WO 98/00526), *Aspergillus lentilus, Aspergillus fumigatus, Aspergillus niger* (U.S. Pat. No. 5,360,901), *Aspergillus oryzae* (JP 2002223772A; U.S. Pat. No. 6,022,721), *Bacillus thermoglucosidasius* (JP 1 1243961A), *Humicola insolens* (WO 2009/104622, WO 2012/130120), *Malbranchea cinnamomea, Microscilla furvescens* (WO 98/00526), *Neurospora crassa, Penicillium emersonii* (WO 2012/130120), *Penicillium pinophilum, Rhizomucor pusillus, Saccharomyces pastorianus* (WO 2007/105350), *Scytalidium thermophilum, Talaromyces stipitatus* (WO 2012/130120), *Thermoascus aurantiacus* (WO 2012/130120), *Thermus brockianus* (WO 2005/044994), and *Thielavia terrestris* (WO 2010/074972).

Non-limiting examples of catalases useful in the present invention are catalases from *Bacillus pseudofirmus* (UNIPROT: P30266), *Bacillus subtilis* (UNIPROT: P42234), *Humicola grisea* (GeneSeqP: AXQ55105), *Neosartorya fischeri* (UNIPROT:A1DJU9), *Penicillium emersonii* (GeneSeqP:BAC10987), *Penicillium pinophilum* (GeneSeqP:BAC10995), *Scytalidium thermophilum* (GeneSeqP: AAW06109 or ADT89624), *Talaromyces stipitatus* (GeneSeqP:BAC10983 or BAC11039; UNIPROT: B8MT74), and *Thermoascus aurantiacus* (GeneSeqP: BAC11005). The accession numbers are incorporated herein in their entirety.

In one aspect, the catalase has a sequence identity to the mature polypeptide of any of the catalases disclosed herein of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have catalase activity.

In another aspect, the amino acid sequence of the catalase differs by up to 10 amino acids, e.g., 1, 2, 3, 4, 5, 6, 7, 8, 9, or 10 from the mature polypeptide of any of the catalases disclosed herein.

In another aspect, the catalase comprises or consists of the amino acid sequence of any of the catalases disclosed herein.

In another aspect, the catalase comprises or consists of the mature polypeptide of any of the catalases disclosed herein.

In another embodiment, the catalase is an allelic variant of a catalase disclosed herein.

In another aspect, the catalase is a fragment containing at least 85% of the amino acid residues, e.g., at least 90% of the amino acid residues or at least 95% of the amino acid residues of the mature polypeptide of a catalase disclosed herein.

In another aspect, the catalase is encoded by a polynucleotide that hybridizes under very low, low, medium, medium-high, high, or very high stringency conditions with the mature polypeptide coding sequence or the full-length complement thereof of any of the catalases disclosed herein (Sambrook et al., 1989, supra).

The polynucleotide encoding a catalase, or a subsequence thereof, as well as the polypeptide of a catalase, or a fragment thereof, may be used to design nucleic acid probes to identify and clone DNA encoding a catalase from strains of different genera or species according to methods well known in the art. In particular, such probes can be used for hybridization with the genomic DNA or cDNA of a cell of interest, as described supra.

For purposes of the present invention, hybridization indicates that the polynucleotide hybridizes to a labeled nucleic acid probe under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of a catalase.

In another aspect, the nucleic acid probe is a polynucleotide that encodes a full-length catalase; the mature polypeptide thereof; or a fragment thereof.

In another aspect, the catalase is encoded by a polynucleotide having a sequence identity to the mature polypeptide coding sequence of any of the catalases disclosed herein of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The catalase may be a hybrid polypeptide in which a region of one polypeptide is fused at the N-terminus or the C-terminus of a region of another polypeptide or a fusion polypeptide or cleavable fusion polypeptide in which another polypeptide is fused at the N-terminus or the C-terminus of the catalase, as described herein.

The protein content of the catalase is in the range of about 0.5% to about 10%, e.g., about 0.5% to about 7%, about 0.5% to about 5%, about 0.5% to about 4%, about 0.5% to about 3%, about 0.5% to about 2%, and about 0.5% to about 1% of total enzyme protein in the saccharification reaction. In an embodiment, the protein ratio of catalase to cellulolytic enzyme composition is in the range of about 1:200 to about 1:10, e.g., about 1:100 to about 1:15 or about 1:50 to about 1:25.

Other Enzymes and Polypeptides Present or Added During Saccharification

Other enzymes and/or polypeptides may be present or added during saccharification. The additional enzymes and/or polypeptide may be added separately or together with the cellulolytic composition and/or GH61 polypeptide.

In an embodiment the cellulolytic enzyme composition comprises or further comprises one or more (several) enzymes and/or polypeptides selected from the group consisting of: hemicellulases, expansins, esterases, laccases, ligninolytic enzymes, pectinases, peroxidases, proteases, and swollenins.

In an embodiment the hemicellulase is a xylanase (e.g., an *Aspergillus aculeatus* xylanase), an acetyxylan esterase, a feruloyl esterase, an arabinofuranosidase, a xylosidase, and a glucuronidase. In a preferred embodiment the hemicellulase is a xylanase and/or a beta-xylosidase.

In an embodiment the xylanase is a GH10 xylanase. In an embodiment the xylanase is derived from a strain of *Aspergillus*, such as a strain of *Aspergillus fumigatus*, such as the one disclosed as Xyl III in WO 2006/078256 or SEQ ID NO: 9 herein, or *Aspergillus aculeatus*, such as the one disclosed in WO 94/21785, e.g., as Xyl II or SEQ ID NO: 8 herein.

In an embodiment the beta-xylosidase is derived from a strain of *Aspergillus*, such as a strain of *Aspergillus fumigatus*, such as the one disclosed in Examples 16-17 as SEQ ID NO: 16 in WO 2013/028928 (hereby incorporated by reference) or SEQ ID NO: 10 herein, or derived from a strain of *Trichoderma*, such as a strain of *Trichoderma reesei*, such as the mature polypeptide of SEQ ID NO: 58 in WO 2011/057140 or SEQ ID NO: 11 herein.

Materials & Methods

Materials:

*Thermoascus aurantiacus* catalase is disclosed in WO 2012/130120.

Cellulolytic Enzyme Composition A:

*Trichoderma reesei* cellulolytic enzyme composition comprising an *Aspergillus fumigatus* Cel7A cellobiohydrolase I (WO 2011/057140), an *Aspergillus fumigatus* cellobiohydrolase II (WO 2011/057140), an *Aspergillus fumigatus* beta-glucosidase variant disclosed in WO 2012/044915 with the following substitutions F100D, S283G, N456E, and F512Y, a *Penicillium* sp. (*emersonii*) GH61 polypeptide (WO 2011/041397), an *Aspergillus fumigatus* GH10 xylanase (WO 2006/078256), and an *Aspergillus fumigatus* beta-xylosidase (WO 2011/057140).

The present invention is further described by the following examples that should not be construed as limiting the scope of the invention.

EXAMPLES

Example 1: Effect of Dissolved Oxygen and Catalase on the Consumption of Titrant In order to investigate the influence of dissolved oxygen and catalase addition on sugar yield and consumption of base titrant, the following experiment was conducted.

The reactor vessels were IKA LR-2.ST reactor systems with anchor stirrers. The vessels were each fitted with one Mettler Toledo InPro 4260 pH and temperature sensor, and one Mettler Toledo InPro 6800 dissolved oxygen and temperature sensor. The sensors were connected to a Mettler Toledo M300 transmitter. The sensor signals were transmitted to a PC. pH was controlled automatically by dosing a 25% (w/w) solution of sodium hydroxide by a peristaltic pump controlled by the PC. Air and nitrogen were introduced to the headspace of the reactors at a rate between 0 and 100 ml/min. The gas flows were regulated by gas mass flow controllers from Cole-Parmer (model#32907-59). The flow of nitrogen was controlled manually, and the flow of air was controlled automatically by the PC on the basis of the dissolved oxygen sensor signal. The following three reactors were run:

(1) Reactor 1. Cellulolytic Enzyme Composition A only with nitrogen blanketing to purge oxygen from the reactor.

(2) Reactor 2. Cellulolytic Enzyme Composition A only with dissolved oxygen (DO) adjustment set to 2% saturation.

(3) Reactor 3. Cellulolytic Enzyme Composition A and *Thermoascus aurantiacus* catalase with DO adjustment set to 2% saturation.

For each of the reactors above, the substrate was steam exploded wheat straw with a dry matter content of 20%. The temperature was set to 50-51° C. with an agitator speed at 75 rpm.

A total of 830 g liquor and 394 ml water were loaded into each reactor. The pH of the liquids was adjusted to 5.2-5.3 with 25% NaOH. The solids were added through a funnel in the top of the reactor under agitation. The pH was maintained at 5.0 for the remainder of the reaction.

The enzyme dose for reactor 1 and reactor 2 was Cellulolytic Enzyme Composition A at 9 mg enzyme protein per g cellulose. The enzyme dose for reactor 3 was Cellulolytic Enzyme Composition A at 8.78 mg enzyme protein per g cellulose plus 0.217 mg/g catalase.

The nitrogen flow was 100 ml/minute initially for all reactors until the dissolved oxygen concentration was below 10% of the saturation level. A nitrogen flow of 10 ml/minute to the headspace was maintained during the trial, in order to protect against exceeding the DO concentration. The dissolved oxygen concentration for reactors 2 and 3 was maintained at 2% of the saturation level for the remainder of the reaction.

Preparation of samples for HPLC: Slurry samples were removed from each of the reactor vessels at 3 and 5 days with a serological pipette and transferred to 15 ml plastic tubes. The samples were centrifuged for 20 minutes at 4000 rpm in a benchtop centrifuge to separate liquids and solids. A total of 300 microliters of supernatant from each sample was diluted with 2.09 ml of DI water and 6 microliters of 40% $H_2SO_4$ (8× dilution). The diluted samples were filtered through 0.45 µm PES syringe filters.

The sugar concentrations of the samples were measured using a 300×7.7 mm HyperREZ XP Carbohydrate H+8 µm column equipped with a 0.2 µm inline filter, in place of a guard column, by elution with 5 mM $H_2SO_4$ as mobile phase at 65° C. at a flow rate of 0.9 ml per minute, and quantitation by integration of the glucose signal from refractive index detection at 50° C. (AGILENT® 1200 HPLC, Agilent Technologies, Santa Clara, Calif., USA) calibrated by sugar standards. The injection volume was 10 microliters and the run time was 18 minutes.

The sugar standard was prepared by adding 8.0000 g of cellobiose, 15.0000 g of glucose, 15.0000 g of xylose, 8.0000 g of arabinose, 8.0000 g of xylitol, 8.0000 g of glycerol. 12.0000 g of sodium acetate, and 15.0000 g of ethanol to a 200 mL class A volumetric flask with 5 mM $H_2SO_4$ to make a stock solution (SS). The following dilutions were made in 5 mM $H_2SO_4$ from the stock solution (SS):

Standard 5=SS
Standard 4=SS diluted 2×
Standard 3=SS diluted 4×
Standard 2=SS diluted 20×
Standard 1=SS diluted 50×
Check Standard=SS diluted 10×

The results are provided in the following tables:

| Amount Glucose Produced (g/l) | | | | | |
|---|---|---|---|---|---|
| Reactor 1 | | Reactor 2 | | Reactor 3 | |
| 3 days | 5 days | 3 days | 5 days | 3 days | 5 days |
| 45.2 | 49.5 | 61.4 | 63.3 | 60.2 | 67.8 |

| Amount Xylose Produced (g/l) | | | | | |
|---|---|---|---|---|---|
| Reactor 1 | | Reactor 2 | | Reactor 3 | |
| 3 days | 5 days | 3 days | 5 days | 3 days | 5 days |
| 23.3 | 23.6 | 24.9 | 25.1 | 24.9 | 26.3 |

The table below shows the amount of base consumed during saccharification to maintain a pH of 5.2 during the reaction.

| Reactor | NaOH (25%, ml) |
|---|---|
| 1: Nitrogen | 4.9 |
| 2: 2% DO | 9.6 |
| 3: catalase + 2% DO | 5.7 |

The results show that a low level of dissolved oxygen (2% saturation) was advantageous for the saccharification process, as compared to anoxic conditions, but that it led to a higher consumption (almost doubling) of base titrant required for maintaining the pH value at the set-point of 5 during the hydrolysis. The data also demonstrates that the addition of catalase together with 2% dissolved oxygen saturation significantly reduced the increase in consumption of titrant and substantially improved the yield of both xylose and glucose after 5 days of incubation.

Example 2

A 5 kg biomass mix consisting of 80% corn stover and 20% cobs was first mixed with 15 liters of 1.3% weight of sulfuric acid. The slurry was pretreated at 125° C. for 120 minutes. The 20 kg total pretreated slurry was pressed mechanically, the liquid was pressed out and collected; and the solid was then washed with 15 liters of water and pressed again. The liquid collected from both pressing steps was mixed. It was about total 20.5 kg, labeled the liquid fraction. The solid after second pressing was subjected to steam explosion at 190° C. for 10 minutes. The collected slurry from steam explosion was about 14.6 kg, labeled the solid fraction. The composition of each stream was analyzed using NREL protocol TP-510-48825, "Laboratory Analytical Procedure (LAP) Review and Integration: Pretreated Slurries" (issued August 2011), and the results are shown in the table below:

| | Solid fraction of acid pretreated corn stover and cobs | Liquid fraction of acid pretreated corn stover and cobs |
|---|---|---|
| Total Solid (%) | 33.60% | 8.66% |
| cellulose/solid | 51.20% | — |
| Xylan/solid | 11.20% | — |
| Density | | 1.021 |

Hydrolysis reactors were 2.5 liter vertical IKA reactors. A 468.28 g of the solid fraction of the acid pretreated corn stover and cobs were weighed into each reactor vessel followed by the addition of 765.19 ml of the liquid stream. Additional water was added to make the slurry about 16.5% total solids. The agitator system was lowered into the reactor vessel and the head plate/lid was closed and secured with a clamp. The head plate also contained tubes for delivering air and NaOH via a peristaltic pump.

The following settings were entered into the computer which controlled the reactor: pH—5.0; temperature—50° C.; agitation speed—75 rpm; and air flow rate—0 or 20 ml/minute. Once the system was started, data acquisition was begun. The system was allowed to automatically adjust the pH to the desired settings. After 3 hours, the pH was at the required setting. Then an enzyme solution was added based on the experimental plan. The final slurry in each reactor had 15% total solids. During hydrolysis, the reactors were monitored for dissolved oxygen (DO), pH, temperature, and mixing speed (rpm).

To sample the reactors, 700 μL of slurry were removed and centrifuged at 14,000 rpm in a Spin-X centrifuge tube for 10 minutes. The filter was discarded and the filtrate was inactivated by addition of 40% sulphuric acid solution (1 μL per 100 μL of sample) and mixing by aspiration. Each inactivated filtrate was dispensed into a tube with a pipette to avoid any solids on the top of the tube. Each inactivated filtrate was diluted 10× with 5 mM sulphuric acid in an HPLC vial (minimum volume: 0.5 mL). The content of glucose was then determined using an Agilent HPLC System equipped with an analytical BIO-RAD Aminex® HPX-87H column and a BIO-RAD Cation H refill guard column Aminex® 87H column for sugar detection.

The DO in the hydrolysis slurry was 0.5-2.0% % of the saturation level after the enzymes were added to the reactors with no air supply or addition. Alternatively, DO was added to the hydrolysis slurry with air flow at a concentration between 3-30% of the saturation level after the enzymes were added to the reactors. The air flow was 20 ml/minute into the head space. All other conditions were kept the same. During hydrolysis, Cellulolytic Enzyme Composition A was dosed at 5 mg enzyme protein per gram cellulose and Thermoacscus *aurantiacus* catalase was dosed at 0.25 mg enzyme protein per gram cellulose. All hydrolysis reactions were performed at 50° C., pH 5.0 and 75 rpm agitation. Enzyme protein concentration was measured using a BCA (B) assay based on EB-SM-0785.02-D, "Validation of Total Protein Measurement for Biomass, colorimetric by Konelab (BCA(B))".

The results are provided in Table 1:

TABLE 1

| Amount Glucose Produced (g/l) | | | | | | | |
|---|---|---|---|---|---|---|---|
| No air addition Cellulolytic Enzyme Composition A | | No air addition Cellulolytic Enzyme Composition A + catalase | | 20 ml/min air Cellulolytic Enzyme Composition A | | 20 ml/min air Cellulolytic Enzyme Composition A + catalase | |
| 3 days | 5 days | 3 days | 5 days | 3 days | 5 days | 3 days | 5 days |
| 41.9 ± 0.3 | 45.6 ± 0.6 | 42.4 ± 0.2 | 45.1 ± 0.6 | 45.7 ± 0.5 | 49.2 ± 0.4 | 47.3 ± 0.5 | 50.3 ± 0.1 |

When no air was supplied, catalase had no effect on the hydrolysis by Cellulolytic Enzyme Composition A. When air was supplied at 20 ml/minute or the DO was between 3-30%, catalase addition boosted the yield of glucose in the hydrolysis with Cellulolytic Enzyme Composition A.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The present invention is further described in the following numbered paragraphs:

1. A method of saccharifying a cellulosic material comprising subjecting the cellulosic material to a cellulolytic enzyme composition, a GH61 polypeptide, and a catalase in a vessel, wherein oxygen is added to the vessel to maintain a concentration of dissolved oxygen of at least 0.5% of the saturation level.

2. A method of saccharifying a cellulosic material comprising subjecting the cellulosic material to a cellulolytic enzyme composition, a GH61 polypeptide, and a catalase in a vessel, wherein oxygen is added to the vessel to maintain a concentration of dissolved oxygen of at least 0.5 ppm, such as, e.g., 0.5 to 5 ppm, 0.5 to 4.5 ppm, 0.5 to 4 ppm, 0.5 to 3.5 ppm, 0.5 to 3 ppm, 0.5 to 2.5 ppm, or 0.5 to 2 ppm.

3. A method of saccharifying a cellulosic material comprising subjecting the cellulosic material to a cellulolytic enzyme composition, a GH61 polypeptide, and a catalase in a vessel, wherein oxygen is added to the vessel to maintain a concentration of dissolved oxygen in the range of 0.025 ppm to 0.55 ppm, such as, e.g., 0.05 to 0.165 ppm.

4. The method of any of paragraphs 1-3, wherein the amount of catalase is in the range of 0.5% to 25%, e.g., 0.5% to 20%, 0.5% to 15%, 0.5% to 10%, 0.5% to 7.5%, 0.5% to 5%, and 0.5% to 4% of total protein.

5. The method of any of paragraphs 1, 3, and 4, wherein the dissolved oxygen concentration during saccharification is in the range of 0.5-10% of the saturation level, such as 0.5-7%, such as 0.5-5%, such as 0.5-4%, such as 0.5-3%, such as 0.5-2%, such as 1-5%, such as 1-4%, such as 1-3%, such as 1-2%.

6. The method of any of paragraphs 1, 3, 4, and 5, wherein the dissolved oxygen concentration is maintained in the range of 0.5-10% of the saturation level, such as 0.5-7%, such as 0.5-5%, such as 0.5-4%, such as 0.5-3%, such as 0.5-2%, such as 1-5%, such as 1-4%, such as 1-3%, such as 1-2% during at least 25%, such as at least 50%, such as at least 75% of the saccharification period.

7. The method of any of paragraphs 1, 2, and 4, wherein the dissolved oxygen concentration during saccharification is in the range of greater than 10% up to 90% of the saturation level, such as greater than 10% up to 80%, greater than 10% up to 70%, greater than 10% up to 60%, greater than 10% up to 50%, greater than 10% up to 40%, greater than 10% up to 30%, and greater than 10% up to 20%.

8. The method of any of paragraphs 1, 2, 4, and 7, wherein the dissolved oxygen concentration is maintained in the range of greater than 10% up to 90% of the saturation level, such as greater than 10% up to 80%, greater than 10% up to 70%, greater than 10% up to 60%, greater than 10% up to 50%, greater than 10% up to 40%, greater than 10% up to 30%, and greater than 10% up to 20% during at least 25%, such as at least 50% or at least 75% of the saccharification period.

9. The method of any of paragraphs 1-8, wherein the cellulosic material is selected from the group consisting of herbaceous material (including energy crops), agricultural residue, wood (including forestry residue), municipal solid waste, waste paper, pulp, and paper mill residue.

10. The method of any of paragraphs 1-9, wherein the cellulosic material is selected from the group consisting of corn stover, wheat straw, bagasse, corn cob, switchgrass, corn fiber, rice straw, miscanthus, arundo, bamboo, orange peel, poplar, pine, aspen, fir, spruce, willow, and eucalyptus.

11. The method of any of paragraphs 1-10, wherein the cellulosic material is pretreated, e.g., by chemical and/or physical pretreatment, such as dilute acid and/or steam explosion pretreatment.

12. The method of any of paragraphs 1-11, wherein the cellulosic material is pretreated corn stover (PCS), such as dilute acid pretreated corn stover.

13. The method of any of paragraphs 1-12, wherein the cellulosic material is unwashed, such as unwashed pretreated corn stover (uwPCS).

14. The method of any of paragraphs 1-13, wherein the saccharification occurs for up to 200 hours, e.g., about 12 to about 96 hours, about 16 to about 72 hours, or about 24 to about 48 hours, such as for at least 12 hours, e.g., at least 24 hours, 36 hours, 48 hours, 60 hours, or 72 hours.

15. The method of any of paragraphs 1-14, wherein the addition of oxygen to the vessel begins after 24-48 hours of saccharification and continues until the end of saccharification.

16. The method of any of paragraphs 1-15, wherein the addition of oxygen occurs throughout the saccharification.

17. The method of any of paragraphs 1-16, wherein the saccharification is a continuous saccharification in which a cellulosic material and a cellulolytic enzymes composition are added at different intervals throughout the saccharification and the hydrolysate is removed at different intervals throughout the saccharification.

18. The method any of paragraphs 1-17, wherein the saccharification is performed at a temperature in the range of about 25° C. to about 75° C., e.g., about 30° C. to about 70° C., about 35° C. to about 65° C., about 40° C. to 60° C., about 45° C. to 55° C., or about 50° C.

19. The method of any of paragraphs 1-18, wherein the saccharification is performed at a pH in the range of about 3.0 to about 9.0, e.g., 3.5 to 6.5, 4.0 to 6.0, 4.5 to 5.5 or about 5.0.

20. The method of paragraph 19, further comprising adding a base to maintain the pH in the range of about 3.0 to about 9.0, e.g., 3.5 to 6.5, 4.0 to 6.0, 4.5 to 5.5 or about 5.0 during the saccharification.

21. The method of paragraph 20, wherein the base is selected from the group consisting of KOH, NaOH, Ca(OH)$_2$, and NH$_4$OH.

22. The method of paragraph 20 or 21, wherein the base is added in an amount of 25-2,500 mmol base per kg dry cellulosic material, such as 25-1000 mmol/kg, 25-500 mmol/kg, 25-250 mmol/kg, 50-200 mmol/kg.

23. The method of any of paragraphs 1-22, wherein the dry solids content during saccharification (e.g., total solids in the cellulosic material) is less than about 30 wt. %, 25 wt. %, 20 wt. %, 15 wt. %, 10 wt. %, 7.5 wt. %, 5 wt. %, 2.5 wt. %, 2 wt. %, 1 wt. %, or 0.5 wt. %, such as between 5 and 30 wt. % or between 10 and 25 wt. %.

24. The method of any of paragraphs 1-23, wherein the cellulolytic enzyme composition is of eukaryotic origin, such as fungal origin, e.g., filamentous origin.

25. The method of any of paragraphs 1-24, wherein the cellulolytic enzyme composition is derived from *Trichoderma* (e.g., *Trichoderma reesei*).

26. The method of any of paragraphs 1-25, wherein the cellulolytic enzyme composition comprises at least a cellobiohydrolase, an endoglucanase, and a beta-glucosidase.

27. The method of any of paragraphs 1-26, wherein the cellulolytic enzyme composition comprises a cellobiohydrolase I, a cellobiohydrolase II, an endoglucanase, and a beta-glucosidase.

28. The method of any of paragraphs 1-26, wherein the cellulolytic enzyme composition comprises a cellobiohydrolase, an endoglucanase, a beta-glucosidase, and a xylanase.

29. The method of any of paragraphs 1-26, wherein the cellulolytic enzyme composition comprises a cellobiohydrolase I, a cellobiohydrolase II, an endoglucanase, a beta-glucosidase, and a xylanase.

30. The method of any of paragraphs 1-26, wherein the cellulolytic enzyme composition comprises a cellobiohydrolase I, a cellobiohydrolase II, an endoglucanase, a beta-glucosidase, a xylanase, and a beta-xylosidase.

31. The method of any of paragraphs 26-30, wherein the cellulolytic enzyme composition further comprises one or more proteins selected from the group consisting of an acetylmannan esterase, an acetylxylan esterase, an arabinanase, an arabinofuranosidase, a CIP, a coumaric acid esterase, an esterase, an expansin, a feruloyl esterase, a galactosidase, a glucuronidase, a glucuronoyl esterase, a laccase, a ligninolytic enzyme, a mannanase, a mannosidase, a pectinase, a peroxidase, a protease, a superoxide dismutase, and a swollenin.

32. The method of any of paragraphs 1-31, wherein the GH61 polypeptide is derived from *Thermoascus*, such as a strain of *Thermoascus aurantiacus*, such as the one described in WO 2005/074656 as SEQ ID NO: 2 or SEQ ID NO: 1 herein; or derived from *Thielavia*, such as a strain of *Thielavia terrestris*, such as the one described in WO 2005/074647 as SEQ ID NO: 7 and SEQ ID NO: 8 or SEQ ID NO: 4 herein; or derived from a strain of *Aspergillus*, such as a strain of *Aspergillus fumigatus*, such as the one described in WO 2010/138754 as SEQ ID NO: 1 and SEQ ID NO: 2 or SEQ ID NO: 3 herein; or a strain of *Penicillium*, such as a strain of *Penicillium emersonii*, such as the one disclosed in WO 2011/041397 or SEQ ID NO: 2 herein.

33. The method of any of paragraphs 1-32, wherein the cellulolytic enzyme composition further comprises a beta-glucosidase, preferably one derived from a strain of *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as one disclosed as SEQ ID NO: 2 in WO 2005/047499 or SEQ ID NO: 5 herein, or an *Aspergillus fumigatus* beta-glucosidase variant disclosed in WO 2012/044915; or a strain of *Penicillium*, such as a strain of

*Penicillium brasilianum* disclosed as SEQ ID NO: 2 in WO 2007/019442, or a strain of *Trichoderma*, such as a strain of *Trichoderma reesei*.

34. The method of any of paragraphs 1-33, wherein the cellulosic enzyme composition further comprises a xylanase, preferably a GH10 xylanase, such as one derived from a strain of *Aspergillus*, such as a strain of *Aspergillus fumigatus*, such as the one disclosed as Xyl III in WO 2006/078256 or SEQ ID NO: 9 herein, or *Aspergillus aculeatus*, such as the one disclosed in WO 94/21785 as Xyl II or SEQ ID NO: 8 herein.

35. The method of any of paragraphs 1-34, wherein the cellulolytic enzyme composition further comprises a beta-xylosidase, such as one derived from a strain of *Aspergillus*, such as a strain of *Aspergillus fumigatus*, such as the one disclosed in co-pending international application no. PCT/US2012/052163 or SEQ ID NO: 10 herein, or derived from a strain of *Trichoderma*, such as a strain of *Trichoderma reesei*, such as the mature polypeptide of SEQ ID NO: 58 in WO 2011/057140 or SEQ ID NO: 11 herein.

36. The method of any of paragraphs 1-35, wherein the cellulolytic enzyme composition further comprises a cellobiohydrolase I (CBH I), such as one derived from a strain of *Aspergillus*, such as a strain of *Aspergillus fumigatus*, such as the Cel7a CBHI disclosed in SEQ ID NO: 6 in WO 2011/057140 or SEQ ID NO: 6 herein, or a strain of *Trichoderma*, such as a strain of *Trichoderma reesei*.

37. The method of any of paragraphs 1-36, wherein the cellulolytic enzyme composition further comprises a cellobiohydrolase II (CBH II), such as one derived from a strain of *Aspergillus*, such as a strain of *Aspergillus fumigatus* disclosed in SEQ ID NO: 7 herein; or a strain of *Trichoderma*, such as *Trichoderma reesei*, or a strain of *Thielavia*, such as a strain of *Thielavia terrestris*, such as cellobiohydrolase II CEL6A from *Thielavia terrestris*.

38. The method of any of paragraphs 1-37, wherein the cellulolytic enzyme composition further comprises a *Trichoderma reesei* cellulase composition and *Thermoascus aurantiacus* GH61A polypeptide (SEQ ID NO: 2 in WO 2005/074656 or SEQ ID NO: 1 herein).

39. The method of any of paragraphs 1-38, wherein the cellulolytic enzyme composition further comprises a beta-glucosidase, such as an *Aspergillus oryzae* beta-glucosidase fusion protein (WO 2008/057637).

40. The method of any of paragraphs 1-39, wherein the cellulolytic enzyme composition is a *Trichoderma reesei* cellulolytic enzyme composition comprising a *Penicillium emersonii* GH61A polypeptide disclosed in WO 2011/041397 or SEQ ID NO: 2 herein.

41. The method of any of paragraphs 1-40, wherein the cellulolytic enzyme composition further comprises a beta-glucosidase, such as an *Aspergillus fumigatus* beta-glucosidase (SEQ ID NO: 2 of WO 2005/047499 or SEQ ID NO: 5 herein), or a variant thereof with the following substitutions: F100D, S283G, N456E, F512Y (using SEQ ID NO: 5 herein for numbering).

42. The method of any of paragraphs 1-41, wherein the cellulolytic enzyme composition is a *Trichoderma reesei* cellulolytic enzyme composition comprising one or more of the following components:

(a) an *Aspergillus fumigatus* cellobiohydrolase I;
(b) an *Aspergillus fumigatus* cellobiohydrolase II;
(c) an *Aspergillus fumigatus* beta-glucosidase or variant thereof with one or more of the following substitutions: F100D, S283G, N456E, F512Y using SEQ ID NO: 5 herein for numbering; and (d) a *Penicillium* sp. GH61 polypeptide; or homologs thereof.

43. The method of any of paragraphs 1-42, wherein the cellulolytic enzyme composition is a *Trichoderma reesei* cellulolytic enzyme composition, comprising a *Thermoascus aurantiacus* GH61A polypeptide (SEQ ID NO: 1 and SEQ ID NO: 2 in WO 2005/074656 or SEQ ID NO: 1 herein), an *Aspergillus oryzae* beta-glucosidase fusion protein (WO 2008/057637), and an *Aspergillus aculeatus* xylanase (Xyl II in WO 94/21785 or SEQ ID NO: 8 herein).

44. The method of any of paragraphs 1-43, wherein the cellulolytic enzyme composition is a *Trichoderma reesei* cellulolytic enzyme composition, comprising a *Thermoascus aurantiacus* GH61A polypeptide (SEQ ID NO: 2 in WO 2005/074656 or SEQ ID NO: 1 herein), an *Aspergillus fumigatus* beta-glucosidase (SEQ ID NO: 2 of WO 2005/047499 or SEQ ID NO: 5 herein) and an *Aspergillus aculeatus* xylanase (Xyl II disclosed in WO 94/21785 or SEQ ID NO: 8 herein).

45. The method of any of paragraphs 1-44, wherein the cellulolytic enzyme composition is a *Trichoderma reesei* cellulolytic enzyme composition, comprising a *Penicillium emersonii* GH61A polypeptide (SEQ ID NO: 2 in WO 2011/041397 or SEQ ID NO: 2 herein), an *Aspergillus fumigatus* beta-glucosidase (disclosed as SEQ ID NO: 2 in WO 2005/047499 or SEQ ID NO: 5 herein), an *Aspergillus fumigatus* xylanase (Xyl III disclosed in WO 2006/078256 or SEQ ID NO: 9 herein) and a beta-xylosidase derived from a strain of *Aspergillus fumigatus* (SEQ ID NO: 10 herein).

46. The method of any of paragraphs 1-45, wherein the cellulolytic enzyme composition is added in an amount of about 0.01 to about 50.0 mg, e.g., about 1 to about 25 mg, such as about 2-10 mg, such as about 4 to about 8 mg protein per g/dry solids (DS) of the cellulosic material.

47. The method of any of paragraphs 1-46, wherein the catalase is a *Thermoascus aurantiacus* catalase.

48. The method of any of paragraphs 1-47, further comprising recovering the saccharified cellulosic material.

49. The method of paragraph 48, wherein the saccharified cellulosic material is a sugar.

50. The method of paragraph 49, wherein the sugar is selected from the group consisting of arabinose, galactose, glucose, mannose, and xylose.

51. The method of any of paragraphs 1-50, wherein the GH61 polypeptide constitutes from 0.1-15%, preferably 0.5-10%, and more preferably 0.5-7% of the cellulolytic enzyme composition.

52. The method of any of paragraphs 1-51, wherein the vessel comprises more than 10 m$^3$, such as more than 25 m$^3$, such as more than 50 m$^3$ cellulosic material.

53. A method of producing a fermentation product from cellulosic material, comprising:

(a) saccharification of the cellulosic material in accordance with the method of any of paragraphs 1-52; and
(b) fermenting the saccharified cellulosic material with one or more fermenting microorganisms.

54. The method of paragraph 53, further comprising recovering the fermentation product from (b).

55. The method of paragraph 53 or 54, wherein the saccharification and fermentation occur simultaneously or sequentially.

56. The method of any of paragraphs 53-55, wherein the fermentation occurs for about 8 to about 96 hours, such as about 24 to about 60 hours.

57. The method of any of paragraphs 53-56, wherein the fermentation is performed at a temperature between about 26° C. to about 60° C., in particular about 32° C. or 50° C.

58. The method of any of paragraphs 53-57, wherein the fermentation is performed at about pH 3 to about pH 8, such as around pH 4-5, 6, or 7.
59. The method of any of paragraphs 53-58, wherein the fermentation product is an alcohol, an organic acid, a ketone, an amino acid, or a gas.
60. The method of paragraph 59, wherein the fermentation product is ethanol.
61. The method of any of paragraphs 53-60, wherein the fermenting microorganism is a bacterial or fungal organism.
62. The method of any of paragraphs 53-61, wherein the fermenting organism is a hexose and/or pentose fermenting organism, or a combination thereof.
63. The method of any of paragraphs 53-62, wherein the fermenting microorganism is a strain of *Saccharomyces* spp., preferably *Saccharomyces cerevisiae*.
64. The method of any of paragraphs 53-63, wherein the fermenting organism is a strain of *Pichia*, preferably *Pichia stipitis*, such as *Pichia stipitis* CBS 5773; strain of *Candida*, preferably *Candida boidinii, Candida brassicae, Candida sheatae, Candida diddensii, Candida pseudotropicalis*, or *Candida utilis*.
65. The method of any of paragraphs 53-64, wherein the fermenting organism is a strain of *Zymomonas*, such as *Zymomonas mobilis*; *Hansenula*, such as *Hansenula anomala*; *Kluyveromyces*, such as *K. marxianus, K. lactis, K. thermotolerans*, and *K. fragilis*; *Schizosaccharomyces*, such as *S. pombe*; *E. coli*, a strain of *Clostridium*, such as *Clostridium acetobutylicum, Chlostridium thermocellum*, and *Chlostridium phytofermentans*; a strain of *Geobacillus* sp.; a strain of *Thermoanaerobacter*, such as *Thermoanaerobacter saccharolyticum*; a strain of *Bacillus*, such as *Bacillus coagulans*.
66. The method of any of paragraphs 53-65, wherein the fermenting microorganism has been genetically modified to provide the ability to ferment pentose sugars, such as xylose utilizing, arabinose utilizing, and xylose and arabinose co-utilizing microorganisms.
67. The method of any of paragraphs 53-66, wherein the fermenting microorganism is a strain of *Saccharomyces* spp., such as *Saccharomyces cerevisiae*, capable of effectively co-fermenting glucose and xylose.
68. The method of any of paragraphs 53-67, wherein the fermenting microorganism expresses xylose isomerase.

The invention claimed is:

1. A method of saccharifying a cellulosic material comprising subjecting the cellulosic material to a cellulolytic enzyme composition, a GH61 polypeptide, and a catalase in a vessel, wherein oxygen is added to the vessel to maintain a concentration of dissolved oxygen of at least 0.5% of the saturation level.

2. A method of saccharifying a cellulosic material comprising subjecting the cellulosic material to a cellulolytic enzyme composition, a GH61 polypeptide, and a catalase in a vessel, wherein oxygen is added to the vessel to maintain a concentration of dissolved oxygen of at least 0.5 ppm.

3. A method of saccharifying a cellulosic material comprising subjecting the cellulosic material to a cellulolytic enzyme composition, a GH61 polypeptide, and a catalase in a vessel, wherein oxygen is added to the vessel to maintain a concentration of dissolved oxygen in the range of 0.025 ppm to 0.55 ppm.

4. The method of claim 1, wherein the amount of catalase is in the range of 0.5% to 25%.

5. The method of claim 1, wherein the dissolved oxygen concentration during saccharification is in the range of 0.5-10% of the saturation level.

6. The method of claim 1, wherein the dissolved oxygen concentration is maintained in the range of 0.5-10% of the saturation level during at least 25% of the saccharification period.

7. The method of claim 1, wherein the dissolved oxygen concentration during saccharification is in the range of greater than 10% up to 90% of the saturation level.

8. The method of claim 1, wherein the dissolved oxygen concentration is maintained in the range of greater than 10% up to 90% of the saturation level during at least 25% of the saccharification period.

9. The method of claim 1, wherein the addition of oxygen occurs throughout the saccharification.

10. The method of claim 1, wherein the saccharification is a continuous saccharification in which a cellulosic material and a cellulolytic enzymes composition are added at different intervals throughout the saccharification and the hydrolysate is removed at different intervals throughout the saccharification.

11. The method of claim 10, further comprising adding a base to maintain the pH in the range of about 3.0 to about 9.0 during the saccharification.

12. The method of claim 11, wherein the base is selected from the group consisting of KOH, NaOH, $Ca(OH)_2$, and $NH_4OH$.

13. The method of claim 11, wherein the base is added in an amount of 25-2,500 mmol base per kg dry cellulosic material.

14. The method of claim 1, further comprising recovering the saccharified cellulosic material.

15. The method of claim 14, wherein the saccharified cellulosic material is a sugar.

16. The method of claim 15, wherein the sugar is selected from the group consisting of arabinose, galactose, glucose, mannose, and xylose.

17. The method of claim 1, wherein the GH61 polypeptide constitutes from 0.1-15% of the cellulolytic enzyme composition.

18. The method of claim 1, wherein the vessel comprises more than 10 $m^3$ cellulosic material.

19. A method of producing a fermentation product from cellulosic material, comprising:
   (a) saccharification of the cellulosic material in accordance with the method of claim 1; and
   (b) fermenting the saccharified cellulosic material with one or more fermenting microorganisms.

20. The method of claim 19, further comprising recovering the fermentation product from (b).

* * * * *

SEQUENCE LISTING

```
<160> NUMBER OF SEQ ID NOS: 11

<210> SEQ ID NO 1
<211> LENGTH: 250
<212> TYPE: PRT
<213> ORGANISM: Thermoascus aurantiacus

<400> SEQUENCE: 1

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
                20                  25                  30

Lys Lys Tyr Tyr Gly Gly Tyr Leu Val Asn Gln Tyr Pro Tyr Met Ser
            35                  40                  45

Asn Pro Pro Glu Val Ile Ala Trp Ser Thr Thr Ala Thr Asp Leu Gly
        50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
                100                 105                 110

Ile Asn Tyr Leu Ala Pro Cys Asn Gly Asp Cys Ser Thr Val Asp Lys
            115                 120                 125

Thr Gln Leu Glu Phe Phe Lys Ile Ala Glu Ser Gly Leu Ile Asn Asp
        130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
210                 215                 220
```

```
Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 2
<211> LENGTH: 253
<212> TYPE: PRT
<213> ORGANISM: Penicillium emersonii

<400> SEQUENCE: 2

Met Leu Ser Ser Thr Arg Thr Leu Ala Phe Thr Gly Leu Ala Gly
1               5                   10                  15

Leu Leu Ser Ala Pro Leu Val Lys Ala His Gly Phe Val Gln Gly Ile
                20                  25                  30

Val Ile Gly Asp Gln Phe Tyr Ser Gly Tyr Ile Val Asn Ser Phe Pro
            35                  40                  45

Tyr Glu Ser Asn Pro Pro Val Ile Gly Trp Ala Thr Thr Ala Thr
50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 3
<211> LENGTH: 326
<212> TYPE: PRT
<213> ORGANISM: Aspergillus fumigatus

<400> SEQUENCE: 3

Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
                20                  25                  30

Tyr Gly Ser Gln Cys Val Arg Leu Pro Ala Ser Asn Ser Pro Val Thr
            35                  40                  45
```

-continued

```
Asn Val Ala Ser Asp Asp Ile Arg Cys Asn Val Gly Thr Ser Arg Pro
 50                  55                  60

Thr Val Lys Cys Pro Val Lys Ala Gly Ser Thr Val Thr Ile Glu Met
 65                  70                  75                  80

His Gln Gln Pro Gly Asp Arg Ser Cys Ala Asn Glu Ala Ile Gly Gly
                 85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255

Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Gly Ser Gly
        275                 280                 285

Cys Thr Ala Ala Lys Tyr Gln Gln Cys Gly Gly Thr Gly Tyr Thr Gly
    290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325
```

<210> SEQ ID NO 4
<211> LENGTH: 452
<212> TYPE: PRT
<213> ORGANISM: Thielavia terrestris

<400> SEQUENCE: 4

```
Met Leu Ala Asn Gly Ala Ile Val Phe Leu Ala Ala Ala Leu Gly Val
 1                   5                  10                  15

Ser Gly His Tyr Thr Trp Pro Arg Val Asn Asp Gly Ala Asp Trp Gln
                 20                  25                  30

Gln Val Arg Lys Ala Asp Asn Trp Gln Asp Asn Gly Tyr Val Gly Asp
             35                  40                  45

Val Thr Ser Pro Gln Ile Arg Cys Phe Gln Ala Thr Pro Ser Pro Ala
         50                  55                  60

Pro Ser Val Leu Asn Thr Thr Ala Gly Ser Thr Val Thr Tyr Trp Ala
 65                  70                  75                  80

Asn Pro Asp Val Tyr His Pro Gly Pro Val Gln Phe Tyr Met Ala Arg
```

```
            85                  90                  95
Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
            115                 120                 125

Trp Pro Ser Thr Gly Lys Ser Ser Phe Ala Val Pro Ile Pro Pro Cys
            130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
            165                 170                 175

Leu Ser Val Thr Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
            195                 200                 205

Tyr Tyr Pro Val Pro Thr Ser Tyr Gln Asn Pro Gly Pro Ala Val Phe
            210                 215                 220

Ser Cys Met Leu Ala Asn Gly Ala Ile Val Phe Leu Ala Ala Ala Leu
225                 230                 235                 240

Gly Val Ser Gly His Tyr Thr Trp Pro Arg Val Asn Asp Gly Ala Asp
            245                 250                 255

Trp Gln Gln Val Arg Lys Ala Asp Asn Trp Gln Asp Asn Gly Tyr Val
            260                 265                 270

Gly Asp Val Thr Ser Pro Gln Ile Arg Cys Phe Gln Ala Thr Pro Ser
            275                 280                 285

Pro Ala Pro Ser Val Leu Asn Thr Thr Ala Gly Ser Thr Val Thr Tyr
            290                 295                 300

Trp Ala Asn Pro Asp Val Tyr His Pro Gly Pro Val Gln Phe Tyr Met
305                 310                 315                 320

Ala Arg Val Pro Asp Gly Glu Asp Ile Asn Ser Trp Asn Gly Asp Gly
            325                 330                 335

Ala Val Trp Phe Lys Val Tyr Glu Asp His Pro Thr Phe Gly Ala Gln
            340                 345                 350

Leu Thr Trp Pro Ser Thr Gly Lys Ser Ser Phe Ala Val Pro Ile Pro
            355                 360                 365

Pro Cys Ile Lys Ser Gly Tyr Tyr Leu Leu Arg Ala Glu Gln Ile Gly
            370                 375                 380

Leu His Val Ala Gln Ser Val Gly Gly Ala Gln Phe Tyr Ile Ser Cys
385                 390                 395                 400

Ala Gln Leu Ser Val Thr Gly Gly Ser Thr Glu Pro Pro Asn Lys
            405                 410                 415

Val Ala Phe Pro Gly Ala Tyr Ser Ala Thr Asp Pro Gly Ile Leu Ile
            420                 425                 430

Asn Ile Tyr Tyr Pro Val Pro Thr Ser Tyr Gln Asn Pro Gly Pro Ala
            435                 440                 445

Val Phe Ser Cys
    450

<210> SEQ ID NO 5
<211> LENGTH: 863
<212> TYPE: PRT
<213> ORGANISM: Aspergillus fumigatus

<400> SEQUENCE: 5
```

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
```

```
                420             425             430
Ala Asn Gly Cys Pro Asp Arg Gly Cys Asp Asn Gly Thr Leu Ala Met
            435             440             445
Ala Trp Gly Ser Gly Thr Ala Asn Phe Pro Tyr Leu Val Thr Pro Glu
            450             455             460
Gln Ala Ile Gln Arg Glu Val Ile Ser Asn Gly Asn Val Phe Ala
465             470             475             480
Val Thr Asp Asn Gly Ala Leu Ser Gln Met Ala Asp Val Ala Ser Gln
            485             490             495
Ser Ser Val Ser Leu Val Phe Val Asn Ala Asp Ser Gly Glu Gly Phe
            500             505             510
Ile Ser Val Asp Gly Asn Glu Gly Asp Arg Lys Asn Leu Thr Leu Trp
            515             520             525
Lys Asn Gly Glu Ala Val Ile Asp Thr Val Val Ser His Cys Asn Asn
            530             535             540
Thr Ile Val Val Ile His Ser Val Gly Pro Val Leu Ile Asp Arg Trp
545             550             555             560
Tyr Asp Asn Pro Asn Val Thr Ala Ile Ile Trp Ala Gly Leu Pro Gly
                565             570             575
Gln Glu Ser Gly Asn Ser Leu Val Asp Val Leu Tyr Gly Arg Val Asn
            580             585             590
Pro Ser Ala Lys Thr Pro Phe Thr Trp Gly Lys Thr Arg Glu Ser Tyr
            595             600             605
Gly Ala Pro Leu Leu Thr Glu Pro Asn Asn Gly Asn Gly Ala Pro Gln
            610             615             620
Asp Asp Phe Asn Glu Gly Val Phe Ile Asp Tyr Arg His Phe Asp Lys
625             630             635             640
Arg Asn Glu Thr Pro Ile Tyr Glu Phe Gly His Gly Leu Ser Tyr Thr
                645             650             655
Thr Phe Gly Tyr Ser His Leu Arg Val Gln Ala Leu Asn Ser Ser Ser
                660             665             670
Ser Ala Tyr Val Pro Thr Ser Gly Glu Thr Lys Pro Ala Pro Thr Tyr
            675             680             685
Gly Glu Ile Gly Ser Ala Ala Asp Tyr Leu Tyr Pro Glu Gly Leu Lys
            690             695             700
Arg Ile Thr Lys Phe Ile Tyr Pro Trp Leu Asn Ser Thr Asp Leu Glu
705             710             715             720
Asp Ser Ser Asp Pro Asn Tyr Gly Trp Glu Asp Ser Glu Tyr Ile
            725             730             735
Pro Glu Gly Ala Arg Asp Gly Ser Pro Gln Pro Leu Leu Lys Ala Gly
            740             745             750
Gly Ala Pro Gly Gly Asn Pro Thr Leu Tyr Gln Asp Leu Val Arg Val
            755             760             765
Ser Ala Thr Ile Thr Asn Thr Gly Asn Val Ala Gly Tyr Glu Val Pro
            770             775             780
Gln Leu Tyr Val Ser Leu Gly Gly Pro Asn Glu Pro Arg Val Val Leu
785             790             795             800
Arg Lys Phe Asp Arg Ile Phe Leu Ala Pro Gly Glu Gln Lys Val Trp
                805             810             815
Thr Thr Thr Leu Asn Arg Arg Asp Leu Ala Asn Trp Asp Val Glu Ala
            820             825             830
Gln Asp Trp Val Ile Thr Lys Tyr Pro Lys Lys Val His Val Gly Ser
            835             840             845
```

```
Ser Ser Arg Lys Leu Pro Leu Arg Ala Pro Leu Pro Arg Val Tyr
    850                 855                 860
```

```
<210> SEQ ID NO 6
<211> LENGTH: 532
<212> TYPE: PRT
<213> ORGANISM: Aspergillus fumigatus

<400> SEQUENCE: 6

Met Leu Ala Ser Thr Phe Ser Tyr Arg Met Tyr Lys Thr Ala Leu Ile
 1               5                  10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
```

```
                355                 360                 365
Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Thr Thr Thr Thr Thr Thr Thr Thr
465                 470                 475                 480

Gln Pro Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530

<210> SEQ ID NO 7
<211> LENGTH: 454
<212> TYPE: PRT
<213> ORGANISM: Aspergillus fumigatus

<400> SEQUENCE: 7

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190
```

-continued

```
Glu Tyr Ser Ile Ala Asn Asn Gly Val Ala Asn Tyr Lys Ala Tyr Ile
            195                 200                 205

Asp Ala Ile Arg Ala Gln Leu Val Lys Tyr Ser Asp Val His Thr Ile
        210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450

<210> SEQ ID NO 8
<211> LENGTH: 344
<212> TYPE: PRT
<213> ORGANISM: Aspergillus aculeatus
<220> FEATURE:
<221> NAME/KEY: SIGNAL
<222> LOCATION: (1)..(22)
<220> FEATURE:
<221> NAME/KEY: mat_peptide
<222> LOCATION: (23)..(344)

<400> SEQUENCE: 8

Met Val Gly Leu Leu Ser Ile Thr Ala Ala Leu Ala Ala Thr Val Leu
            -20                 -15                 -10

Pro Asn Ile Val Ser Ala Val Gly Leu Asp Gln Ala Ala Val Ala Lys
        -5                  -1 1                 5                  10

Gly Leu Gln Tyr Phe Gly Thr Ala Thr Asp Asn Pro Glu Leu Thr Asp
                15                  20                  25

Ile Pro Tyr Val Thr Gln Leu Asn Asn Thr Ala Asp Phe Gly Gln Ile
            30                  35                  40

Thr Pro Gly Asn Ser Met Lys Trp Asp Ala Thr Glu Pro Ser Gln Gly
        45                  50                  55
```

```
Thr Phe Thr Phe Thr Lys Gly Asp Val Ile Ala Asp Leu Ala Glu Gly
            60                  65                  70

Asn Gly Gln Tyr Leu Arg Cys His Thr Leu Val Trp Tyr Asn Gln Leu
 75                  80                  85                  90

Pro Ser Trp Val Thr Ser Gly Thr Trp Thr Asn Ala Thr Leu Thr Ala
                 95                 100                 105

Ala Leu Lys Asn His Ile Thr Asn Val Val Ser His Tyr Lys Gly Lys
            110                 115                 120

Cys Leu His Trp Asp Val Val Asn Glu Ala Leu Asn Asp Asp Gly Thr
            125                 130                 135

Tyr Arg Thr Asn Ile Phe Tyr Thr Thr Ile Gly Glu Ala Tyr Ile Pro
        140                 145                 150

Ile Ala Phe Ala Ala Ala Ala Ala Asp Pro Asp Ala Lys Leu Phe
155                 160                 165                 170

Tyr Asn Asp Tyr Asn Leu Glu Tyr Gly Gly Ala Lys Ala Ala Ser Ala
                175                 180                 185

Arg Ala Ile Val Gln Leu Val Lys Asn Ala Gly Ala Lys Ile Asp Gly
            190                 195                 200

Val Gly Leu Gln Ala His Phe Ser Val Gly Thr Val Pro Ser Thr Ser
        205                 210                 215

Ser Leu Val Ser Val Leu Gln Ser Phe Thr Ala Leu Gly Val Glu Val
220                 225                 230

Ala Tyr Thr Glu Ala Asp Val Arg Ile Leu Leu Pro Thr Thr Ala Thr
235                 240                 245                 250

Thr Leu Ala Gln Gln Ser Ser Asp Phe Gln Ala Leu Val Gln Ser Cys
                255                 260                 265

Val Gln Thr Thr Gly Cys Val Gly Phe Thr Ile Trp Asp Trp Thr Asp
            270                 275                 280

Lys Tyr Ser Trp Val Pro Ser Thr Phe Ser Gly Tyr Gly Ala Ala Leu
        285                 290                 295

Pro Trp Asp Glu Asn Leu Val Lys Lys Pro Ala Tyr Asn Gly Leu Leu
300                 305                 310

Ala Gly Met Gly Val Thr Val Thr
315                 320

<210> SEQ ID NO 9
<211> LENGTH: 397
<212> TYPE: PRT
<213> ORGANISM: Aspergillus fumigatus

<400> SEQUENCE: 9

Met Val His Leu Ser Ser Leu Ala Ala Ala Leu Ala Ala Leu Pro Leu
1               5                  10                  15

Val Tyr Gly Ala Gly Leu Asn Thr Ala Ala Lys Ala Lys Gly Leu Lys
                20                  25                  30

Tyr Phe Gly Ser Ala Thr Asp Asn Pro Glu Leu Thr Asp Ser Ala Tyr
            35                  40                  45

Val Ala Gln Leu Ser Asn Thr Asp Asp Phe Gly Gln Ile Thr Pro Gly
 50                  55                  60

Asn Ser Met Lys Trp Asp Ala Thr Glu Pro Ser Gln Asn Ser Phe Ser
 65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
```

-continued

```
                100             105             110
        Val Ser Ser Gly Ser Trp Thr Asn Ala Thr Leu Leu Ala Ala Met Lys
                    115             120             125

Asn His Ile Thr Asn Val Val Thr His Tyr Lys Gly Lys Cys Tyr Ala
            130             135             140

Trp Asp Val Val Asn Glu Ala Leu Asn Glu Asp Gly Thr Phe Arg Asn
        145             150             155             160

Ser Val Phe Tyr Gln Ile Ile Gly Pro Ala Tyr Ile Pro Ile Ala Phe
                        165             170             175

Ala Thr Ala Ala Ala Ala Asp Pro Asp Val Lys Leu Tyr Tyr Asn Asp
                    180             185             190

Tyr Asn Ile Glu Tyr Ser Gly Ala Lys Ala Thr Ala Ala Gln Asn Ile
                195             200             205

Val Lys Met Ile Lys Ala Tyr Gly Ala Lys Ile Asp Gly Val Gly Leu
            210             215             220

Gln Ala His Phe Ile Val Gly Ser Thr Pro Ser Gln Ser Asp Leu Thr
        225             230             235             240

Thr Val Leu Lys Gly Tyr Thr Ala Leu Gly Val Glu Val Ala Tyr Thr
                        245             250             255

Glu Leu Asp Ile Arg Met Gln Leu Pro Ser Thr Ala Ala Lys Leu Ala
                    260             265             270

Gln Gln Ser Thr Asp Phe Gln Gly Val Ala Ala Ala Cys Val Ser Thr
                275             280             285

Thr Gly Cys Val Gly Val Thr Ile Trp Asp Trp Thr Asp Lys Tyr Ser
            290             295             300

Trp Val Pro Ser Val Phe Gln Gly Tyr Gly Ala Pro Leu Pro Trp Asp
        305             310             315             320

Glu Asn Tyr Val Lys Lys Pro Ala Tyr Asp Gly Leu Met Ala Gly Leu
                        325             330             335

Gly Ala Ser Gly Ser Gly Thr Thr Thr Thr Thr Thr Thr Thr Ser Thr
                    340             345             350

Thr Thr Gly Gly Thr Asp Pro Thr Gly Val Ala Gln Lys Trp Gly Gln
                355             360             365

Cys Gly Gly Ile Gly Trp Thr Gly Pro Thr Thr Cys Val Ser Gly Thr
            370             375             380

Thr Cys Gln Lys Leu Asn Asp Trp Tyr Ser Gln Cys Leu
        385             390             395

<210> SEQ ID NO 10
<211> LENGTH: 792
<212> TYPE: PRT
<213> ORGANISM: Aspergillus fumigatus

<400> SEQUENCE: 10

Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
                20                  25                  30

Ala Asn Pro Asp Leu Thr Pro Gln Ser Val Ala Thr Ile Asp Leu Ser
            35                  40                  45

Phe Pro Asp Cys Glu Asn Gly Pro Leu Ser Lys Thr Leu Val Cys Asp
        50                  55                  60

Thr Ser Ala Arg Pro His Asp Arg Ala Ala Leu Val Ser Met Phe
65                  70                  75                  80
```

```
Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
    130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
    210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
            260                 265                 270

Met Cys Ser Tyr Asn Ala Val Asn Gly Val Pro Ser Cys Ala Asn Ser
        275                 280                 285

Phe Phe Leu Gln Thr Leu Leu Arg Asp Thr Phe Gly Phe Val Glu Asp
    290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Ala Asp Ser Ile Arg
                325                 330                 335

Ala Gly Thr Asp Ile Asp Cys Gly Thr Thr Tyr Gln Tyr Tyr Phe Gly
            340                 345                 350

Glu Ala Phe Asp Glu Gln Glu Val Thr Arg Ala Glu Ile Glu Arg Gly
        355                 360                 365

Val Ile Arg Leu Tyr Ser Asn Leu Val Arg Leu Gly Tyr Phe Asp Gly
    370                 375                 380

Asn Gly Ser Val Tyr Arg Asp Leu Thr Trp Asn Asp Val Thr Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Lys Ser Val Arg Ser Val
            420                 425                 430

Ala Leu Ile Gly Pro Trp Met Asn Val Thr Thr Gln Leu Gln Gly Asn
        435                 440                 445

Tyr Phe Gly Pro Ala Pro Tyr Leu Ile Ser Pro Leu Asn Ala Phe Gln
    450                 455                 460

Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                485                 490                 495

Asp Val Ile Ile Phe Ala Gly Gly Ile Asp Asn Thr Leu Glu Ala Glu
```

```
                500             505             510
Ala Met Asp Arg Met Asn Ile Thr Trp Pro Gly Asn Gln Leu Gln Leu
            515                 520             525

Ile Asp Gln Leu Ser Gln Leu Gly Lys Pro Leu Ile Val Leu Gln Met
        530                 535             540

Gly Gly Gly Gln Val Asp Ser Ser Leu Lys Ser Asn Lys Asn Val
545                 550             555             560

Asn Ser Leu Ile Trp Gly Gly Tyr Pro Gly Gln Ser Gly Gly Gln Ala
                565             570             575

Leu Leu Asp Ile Ile Thr Gly Lys Arg Ala Pro Ala Gly Arg Leu Val
            580                 585             590

Val Thr Gln Tyr Pro Ala Glu Tyr Ala Thr Gln Phe Pro Ala Thr Asp
        595                 600             605

Met Ser Leu Arg Pro His Gly Asn Asn Pro Gly Gln Thr Tyr Met Trp
        610                 615             620

Tyr Thr Gly Thr Pro Val Tyr Glu Phe Gly His Gly Leu Phe Tyr Thr
625                 630             635             640

Thr Phe His Ala Ser Leu Pro Gly Thr Gly Lys Asp Lys Thr Ser Phe
                645             650             655

Asn Ile Gln Asp Leu Leu Thr Gln Pro His Pro Gly Phe Ala Asn Val
            660                 665             670

Glu Gln Met Pro Leu Leu Asn Phe Thr Val Thr Ile Thr Asn Thr Gly
            675                 680             685

Lys Val Ala Ser Asp Tyr Thr Ala Met Leu Phe Ala Asn Thr Thr Ala
        690                 695             700

Gly Pro Ala Pro Tyr Pro Asn Lys Trp Leu Val Gly Phe Asp Arg Leu
705                 710             715             720

Ala Ser Leu Glu Pro His Arg Ser Gln Thr Met Thr Ile Pro Val Thr
                725             730             735

Ile Asp Ser Val Ala Arg Thr Asp Glu Ala Gly Asn Arg Val Leu Tyr
            740                 745             750

Pro Gly Lys Tyr Glu Leu Ala Leu Asn Asn Glu Arg Ser Val Val Leu
        755                 760             765

Gln Phe Val Leu Thr Gly Arg Glu Ala Val Ile Phe Lys Trp Pro Val
        770                 775             780

Glu Gln Gln Gln Ile Ser Ser Ala
785                 790

<210> SEQ ID NO 11
<211> LENGTH: 797
<212> TYPE: PRT
<213> ORGANISM: Trichoderma reesei

<400> SEQUENCE: 11

Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80
```

-continued

```
Thr Leu Glu Glu Leu Ile Leu Asn Thr Gln Asn Ser Gly Pro Gly Val
                 85                  90                  95
Pro Arg Leu Gly Leu Pro Asn Tyr Gln Val Trp Asn Glu Ala Leu His
            100                 105                 110
Gly Leu Asp Arg Ala Asn Phe Ala Thr Lys Gly Gly Gln Phe Glu Trp
        115                 120                 125
Ala Thr Ser Phe Pro Met Pro Ile Leu Thr Thr Ala Ala Leu Asn Arg
    130                 135                 140
Thr Leu Ile His Gln Ile Ala Asp Ile Ile Ser Thr Gln Ala Arg Ala
145                 150                 155                 160
Phe Ser Asn Ser Gly Arg Tyr Gly Leu Asp Val Tyr Ala Pro Asn Val
                165                 170                 175
Asn Gly Phe Arg Ser Pro Leu Trp Gly Arg Gly Gln Glu Thr Pro Gly
            180                 185                 190
Glu Asp Ala Phe Phe Leu Ser Ser Ala Tyr Thr Tyr Glu Tyr Ile Thr
        195                 200                 205
Gly Ile Gln Gly Gly Val Asp Pro Glu His Leu Lys Val Ala Ala Thr
    210                 215                 220
Val Lys His Phe Ala Gly Tyr Asp Leu Glu Asn Trp Asn Asn Gln Ser
225                 230                 235                 240
Arg Leu Gly Phe Asp Ala Ile Ile Thr Gln Gln Asp Leu Ser Glu Tyr
                245                 250                 255
Tyr Thr Pro Gln Phe Leu Ala Ala Arg Tyr Ala Lys Ser Arg Ser
            260                 265                 270
Leu Met Cys Ala Tyr Asn Ser Val Asn Gly Val Pro Ser Cys Ala Asn
        275                 280                 285
Ser Phe Phe Leu Gln Thr Leu Leu Arg Glu Ser Trp Gly Phe Pro Glu
    290                 295                 300
Trp Gly Tyr Val Ser Ser Asp Cys Asp Ala Val Tyr Asn Val Phe Asn
305                 310                 315                 320
Pro His Asp Tyr Ala Ser Asn Gln Ser Ser Ala Ala Ser Ser Leu
                325                 330                 335
Arg Ala Gly Thr Asp Ile Asp Cys Gly Gln Thr Tyr Pro Trp His Leu
            340                 345                 350
Asn Glu Ser Phe Val Ala Gly Glu Val Ser Arg Gly Glu Ile Glu Arg
        355                 360                 365
Ser Val Thr Arg Leu Tyr Ala Asn Leu Val Arg Leu Gly Tyr Phe Asp
    370                 375                 380
Lys Lys Asn Gln Tyr Arg Ser Leu Gly Trp Lys Asp Val Val Lys Thr
385                 390                 395                 400
Asp Ala Trp Asn Ile Ser Tyr Glu Ala Ala Val Glu Gly Ile Val Leu
                405                 410                 415
Leu Lys Asn Asp Gly Thr Leu Pro Leu Ser Lys Lys Val Arg Ser Ile
            420                 425                 430
Ala Leu Ile Gly Pro Trp Ala Asn Ala Thr Thr Gln Met Gln Gly Asn
        435                 440                 445
Tyr Tyr Gly Pro Ala Pro Tyr Leu Ile Ser Pro Leu Glu Ala Ala Lys
    450                 455                 460
Lys Ala Gly Tyr His Val Asn Phe Glu Leu Gly Thr Glu Ile Ala Gly
465                 470                 475                 480
Asn Ser Thr Thr Gly Phe Ala Lys Ala Ile Ala Ala Lys Lys Ser
                485                 490                 495
Asp Ala Ile Ile Tyr Leu Gly Gly Ile Asp Asn Thr Ile Glu Gln Glu
```

```
                    500                 505                 510
Gly Ala Asp Arg Thr Asp Ile Ala Trp Pro Gly Asn Gln Leu Asp Leu
            515                 520                 525

Ile Lys Gln Leu Ser Glu Val Gly Lys Pro Leu Val Val Leu Gln Met
        530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
        610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
            645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
            675                 680                 685

Lys Thr Glu Ser Pro Tyr Thr Ala Met Leu Phe Val Arg Thr Ser Asn
        690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
            725                 730                 735

Pro Val Ser Ala Leu Ala Arg Val Asp Ser His Gly Asn Arg Ile Val
                740                 745                 750

Tyr Pro Gly Lys Tyr Glu Leu Ala Leu Asn Thr Asp Glu Ser Val Lys
            755                 760                 765

Leu Glu Phe Glu Leu Val Gly Glu Glu Val Thr Ile Glu Asn Trp Pro
        770                 775                 780

Leu Glu Glu Gln Gln Ile Lys Asp Ala Thr Pro Asp Ala
785                 790                 795
```